United States Patent
Stager et al.

(10) Patent No.: US 10,729,444 B2
(45) Date of Patent: Aug. 4, 2020

(54) LIQUID-IMMUNE TRIGGER CIRCUIT FOR SURGICAL INSTRUMENT

(71) Applicant: ETHICON LLC, Guaynabo, PR (US)

(72) Inventors: William R. Stager, Oakwood, OH (US); Timothy E. Goode, Springboro, OH (US)

(73) Assignee: Ethicon LLC, Guaynabo, PR (US)

( * ) Notice: Subject to any disclaimer, the term of this patent is extended or adjusted under 35 U.S.C. 154(b) by 477 days.

(21) Appl. No.: 15/581,640

(22) Filed: Apr. 28, 2017

(65) Prior Publication Data

US 2018/0310939 A1  Nov. 1, 2018

(51) Int. Cl.
  *A61B 17/00*  (2006.01)
  *A61B 17/115*  (2006.01)
  *A61B 90/00*  (2016.01)

(52) U.S. Cl.
  CPC .. *A61B 17/1155* (2013.01); *A61B 2017/00017* (2013.01); *A61B 2017/00115* (2013.01); *A61B 2017/00119* (2013.01); *A61B 2017/00199* (2013.01); *A61B 2017/00367* (2013.01); *A61B 2017/00398* (2013.01); *A61B 2017/00477* (2013.01); *A61B 2017/00734* (2013.01); *A61B 2090/0808* (2016.02); *A61B 2090/0811* (2016.02)

(58) Field of Classification Search
  CPC .......................... A61B 17/1155; A61B 17/072
  USPC ....................................................... 227/175.1
  See application file for complete search history.

(56) References Cited

U.S. PATENT DOCUMENTS

| 5,205,459 A | 4/1993 | Brinkerhoff et al. |
| 5,271,544 A | 12/1993 | Fox et al. |
| 5,275,322 A | 1/1994 | Wolf et al. |
| 5,285,945 A | 2/1994 | Brinkerhoff et al. |
| 5,292,053 A | 3/1994 | Smith et al. |
| 5,333,773 A | 8/1994 | Main et al. |
| 5,350,104 A | 9/1994 | Main et al. |

(Continued)

FOREIGN PATENT DOCUMENTS

| CA | 2975797 A1 | 11/2007 |
| EP | 3 108 826 A2 | 12/2016 |

OTHER PUBLICATIONS

U.S. Appl. No. 15/350,513, filed Nov. 14, 2016.

(Continued)

*Primary Examiner* — Chelsea E Stinson
(74) *Attorney, Agent, or Firm* — Frost Brown Todd LLC

(57) ABSTRACT

An apparatus includes a body, a shaft assembly, an end effector, an activation circuit, and a user input feature. The activation circuit includes an end effector driver and a driver activation switch. The end effector driver is operable to drive the end effector to perform an operation on tissue. The driver activation switch is configured to transition between an open state and a closed state. The end effector driver is configured to activate in response to the driver activation switch transitioning to the open state. The user input feature is operable to transition between a non-actuated state and an actuated state. The driver activation switch remains in the closed state when the user input feature is in the non-actuated state. The driver activation switch is configured to transition to the open state in response to the user input feature transitioning from the non-actuated state to the actuated state.

20 Claims, 20 Drawing Sheets

(56) References Cited

U.S. PATENT DOCUMENTS

| | | | |
|---|---|---|---|
| 5,533,661 A | 7/1996 | Main et al. | |
| 6,945,444 B2 * | 9/2005 | Gresham | A61B 17/115 227/175.1 |
| 7,794,475 B2 | 9/2010 | Hess et al. | |
| 8,910,847 B2 | 12/2014 | Nalagatla et al. | |
| 9,289,207 B2 | 3/2016 | Shelton | |
| 9,463,022 B2 | 10/2016 | Swayze et al. | |
| 9,572,573 B2 | 2/2017 | Scheib et al. | |
| 9,597,081 B2 | 3/2017 | Swayze et al. | |
| 10,405,855 B2 * | 9/2019 | Stager | A61B 17/0644 |
| 10,517,602 B2 * | 12/2019 | Dinardo | A61B 17/1114 |
| 2007/0049121 A1 * | 3/2007 | Steele | B60R 16/0231 439/630 |
| 2008/0223904 A1 * | 9/2008 | Marczyk | A61B 17/068 227/176.1 |
| 2011/0006101 A1 | 1/2011 | Hall et al. | |
| 2012/0253329 A1 * | 10/2012 | Zemlok | A61B 17/072 606/1 |
| 2014/0151430 A1 | 6/2014 | Scheib et al. | |
| 2014/0158747 A1 | 6/2014 | Measamer et al. | |
| 2015/0083772 A1 | 3/2015 | Miller et al. | |
| 2015/0083773 A1 | 3/2015 | Measamer et al. | |
| 2015/0083774 A1 | 3/2015 | Measamer et al. | |
| 2015/0083775 A1 | 3/2015 | Leimbach et al. | |
| 2016/0100837 A1 | 4/2016 | Huang et al. | |
| 2016/0374666 A1 | 12/2016 | DiNardo et al. | |
| 2016/0374667 A1 | 12/2016 | Miller et al. | |
| 2016/0374672 A1 | 12/2016 | Bear et al. | |
| 2017/0086848 A1 | 3/2017 | Miller et al. | |

OTHER PUBLICATIONS

U.S. Appl. No. 15/581,546, filed Apr. 28, 2017.
European Search Report and Written Opinion dated Jul. 16, 2018 for Application No. EP 18169862.2, 7 pgs.
International Search Report and Written Opinion dated Jul. 25, 2018 for Application No. PCT/US2018/028135, 14 pgs.

* cited by examiner

LIQUID-IMMUNE TRIGGER CIRCUIT FOR SURGICAL INSTRUMENT

BACKGROUND

In some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis. The end-to-end anastomosis may provide a substantially unobstructed flow path from one portion of the digestive tract to the other portion of the digestive tract, without also providing any kind of leaking at the site of the anastomosis.

One example of an instrument that may be used to provide an end-to-end anastomosis is a circular stapler. Some such staplers are operable to clamp down on layers of tissue, cut through the clamped layers of tissue, and drive staples through the clamped layers of tissue to substantially seal the layers of tissue together near the severed ends of the tissue layers, thereby joining the two severed ends of the anatomical lumen together. The circular stapler may be configured to sever the tissue and seal the tissue substantially simultaneously. For instance, the circular stapler may sever excess tissue that is interior to an annular array of staples at an anastomosis, to provide a substantially smooth transition between the anatomical lumen sections that are joined at the anastomosis. Circular staplers may be used in open procedures or in endoscopic procedures. In some instances, a portion of the circular stapler is inserted through a patient's naturally occurring orifice.

Examples of circular staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910, 847, entitled "Low Cost Anvil Assembly for a Circular Stapler," issued Dec. 16, 2014. The disclosure of each of the above-cited U.S. patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015, now abandoned; U.S. Pub. No. 2015/0083773, entitled "Surgical Stapling Instrument with Drive Assembly Having Toggle Features," published Mar. 26, 2015, issued as U.S. Pat. No. 9,936,949 on Apr. 10, 2018; U.S. Pub. No. 2015/0083774, entitled "Control Features for Motorized Surgical Stapling Instrument," published Mar. 26, 2015, issued as U.S. Pat. No. 9,907,552 on Mar. 6, 2018; and U.S. Pub. No. 2015/0083775, entitled "Surgical Stapler with Rotary Cam Drive," published Mar. 26, 2015, issued as U.S. Pat. No. 9,713,469 on Jul. 25, 2017. The disclosure of each of the above-cited U.S. patent Publications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
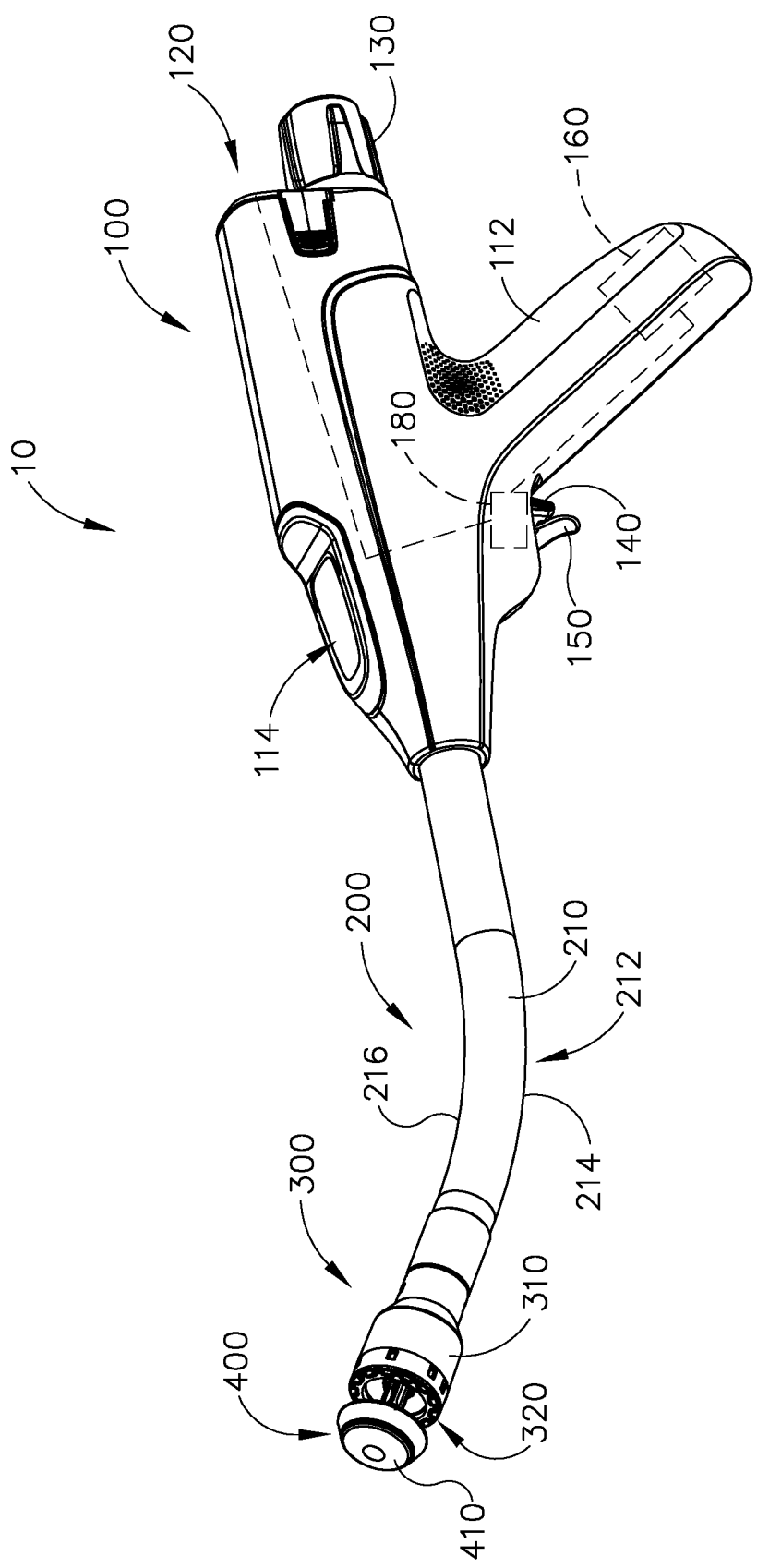
FIG. 1 depicts a perspective view of an exemplary circular stapler.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

Figure 2:
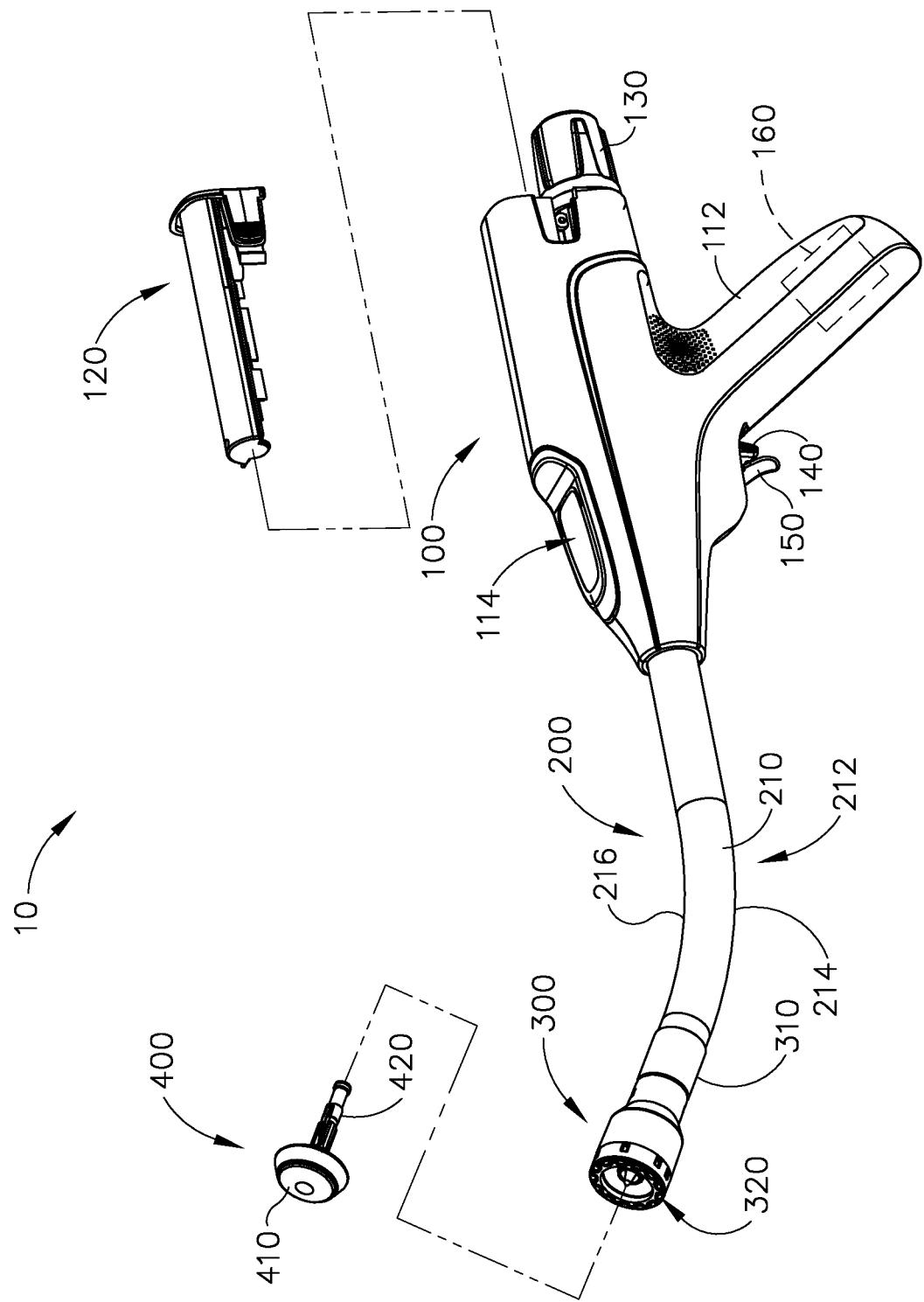
FIG. 2 depicts a perspective view of the circular stapler of FIG. 1, with a battery pack removed from a handle assembly and an anvil removed from a stapling head assembly.

FIGS. 1-2 depict an exemplary surgical circular stapling instrument (10) that may be used to provide an end-to-end anastomosis between two sections of an anatomical lumen such as a portion of a patient's digestive tract. Instrument (10) of this example comprises a handle assembly (100), a shaft assembly (200), a stapling head assembly (300), an anvil (400), and a removable battery pack (120). Each of these components will be described in greater detail below. It should be understood that, in addition to or in lieu of the following, instrument (10) may be further constructed and operable in accordance with at least some of the teachings of U.S. Pub. No. 2016/0374672, entitled "Method of Applying an Annular Array of Staples to Tissue," published Dec. 29, 2016, issued as U.S. Pat. No. 10,478,189 on Nov. 19, 2019; U.S. Pat. Nos. 5,205,459; 5,271,544; 5,275,322; 5,285,945; 5,292,053; 5,333,773; 5,350,104; 5,533,661; and/or U.S. Pat. No. 8,910,847, the disclosures of which are incorporated by reference herein. Still other suitable configurations will be apparent to one of ordinary skill in the art in view of the teachings herein.

A. Exemplary Tissue Engagement Features of Circular Stapling Instrument

Figure 3:
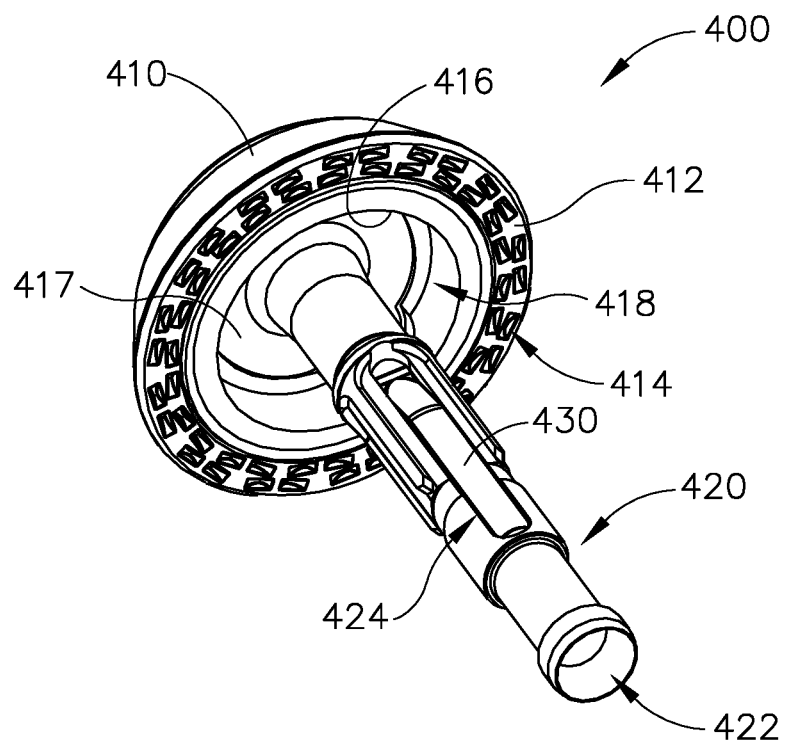
FIG. 3 depicts a perspective view of the anvil of the circular stapler of FIG. 1.

As best seen in FIG. 3, anvil (400) of the present example comprises a head (410) and a shank (420). Head (410) includes a proximal surface (412) that defines a plurality of staple forming pockets (414). Staple forming pockets (414) are arranged in two concentric annular arrays in the present example. Staple forming pockets (414) are configured to deform staples as the staples are driven into staple forming pockets (414) (e.g., deforming a generally "U" shaped staple into a "B" shape as is known in the art). Shank (420) defines a bore or lumen (422) and includes a pair of pivoting latch members (430) positioned in bore (422). Each latch member (430) includes features that allows anvil (400) to be removably secured to a trocar (330) of stapling head assembly (300) as will be described in greater detail below. It should be understood, however, that anvil (400) may be removably secured to a trocar (330) using any other suitable components, features, or techniques.

Figure 4:
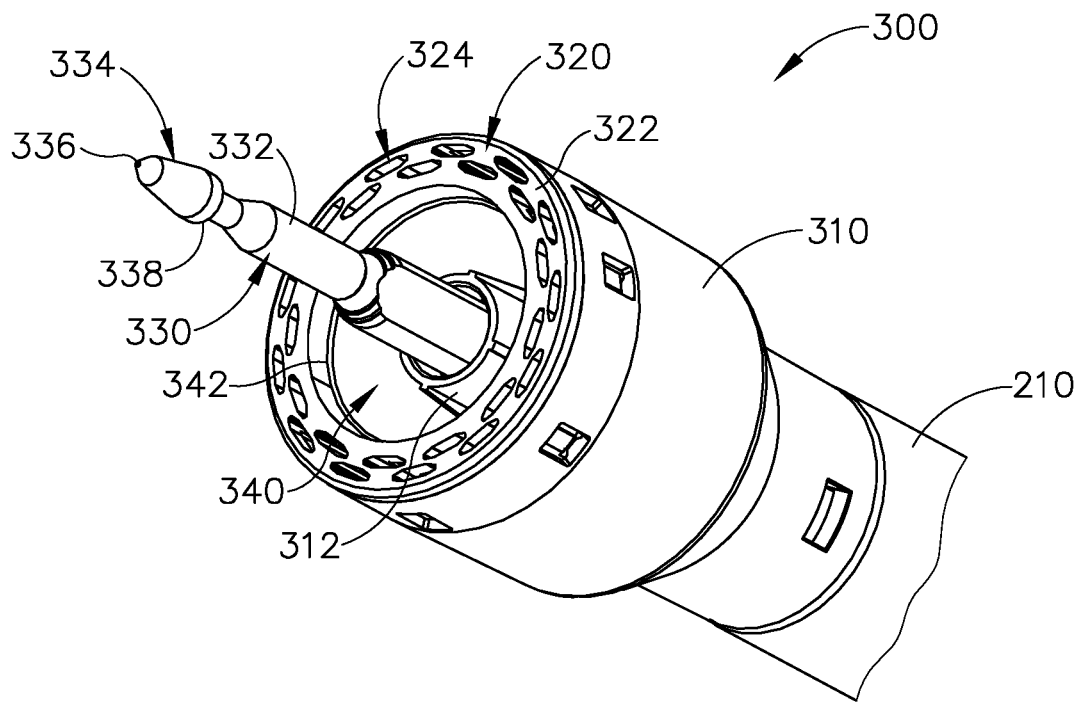
FIG. 4 depicts a perspective view of the stapling head assembly of the circular stapler of FIG. 1.
Figure 5:
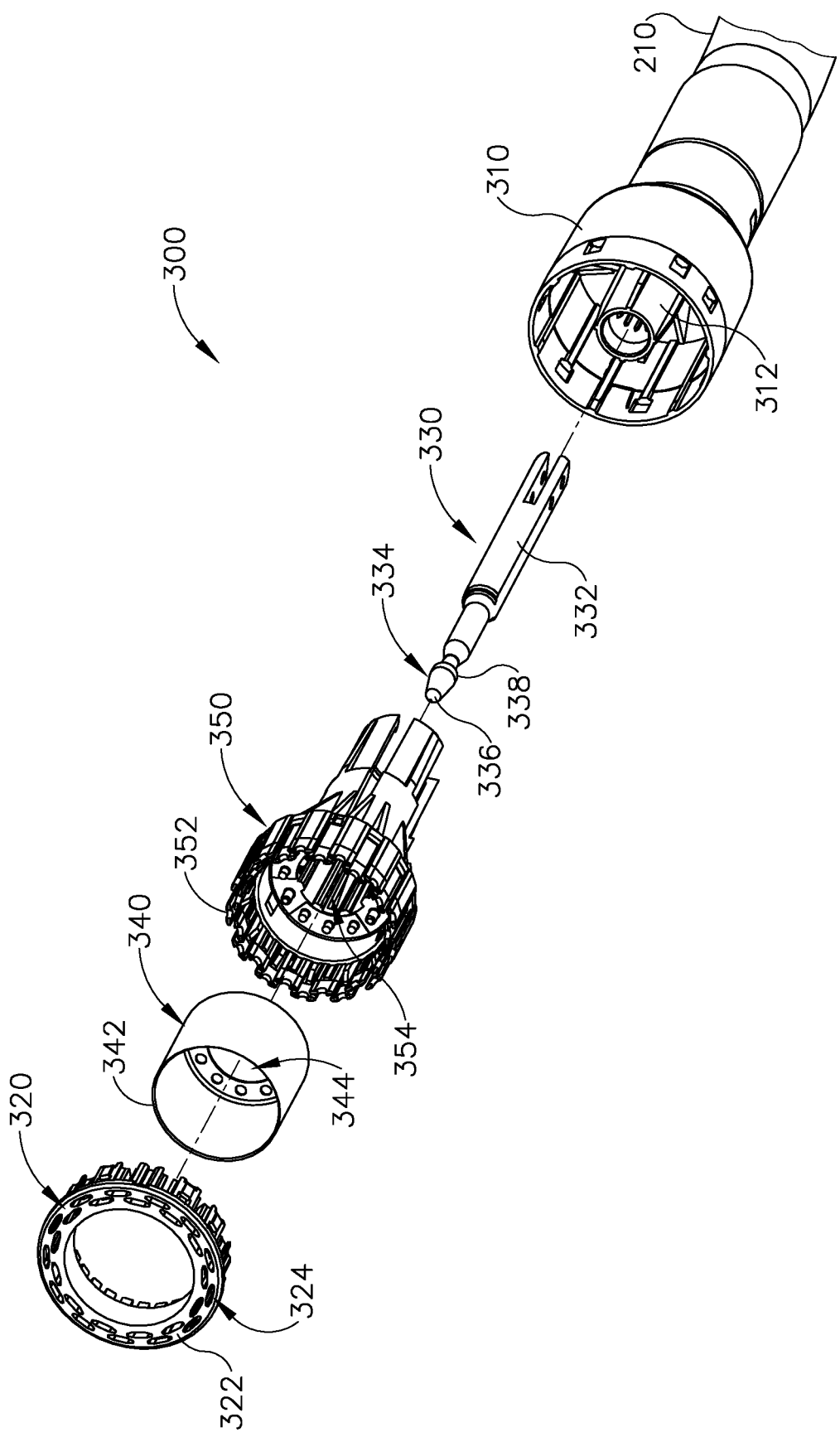
FIG. 5 depicts an exploded perspective view of the stapling head assembly of FIG. 4.

Stapling head assembly (300) is located at the distal end of shaft assembly (200). As shown in FIGS. 1-2, anvil (400) is configured to removably couple with shaft assembly (200), adjacent to stapling head assembly (300). As will be described in greater detail below, anvil (400) and stapling head assembly (300) are configured to cooperate to manipulate tissue in three ways, including clamping the tissue, cutting the tissue, and stapling the tissue. As best seen in FIGS. 4-5, stapling head assembly (300) of the present example comprises a tubular casing (310) housing a slidable staple driver member (350). A cylindraceous inner core member (312) extends distally within tubular casing (310). Tubular casing (310) is fixedly secured to an outer sheath (210) of shaft assembly (200), such that tubular casing (310) serves as a mechanical ground for stapling head assembly (300).

Trocar (330) is positioned coaxially within inner core member (312) of tubular casing (310). Trocar (330) is operable to translate distally and proximally relative to tubular casing (310) in response to rotation of a knob (130) located at the proximal end of handle assembly (100). Trocar (330) comprises a shaft (332) and a head (334). Head (334) includes a pointed tip (336) and an inwardly extending proximal surface (338). Head (334) and the distal portion of shaft (332) are configured for insertion in bore (422) of anvil (420). Proximal surface (338) is configured to complement features of latch members (430) to provide a snap fit between anvil (400) and trocar (330).

Staple driver member (350) is operable to actuate longitudinally within tubular casing (310) in response to activation of motor (160) as will be described in greater detail below. Staple driver member (350) includes two distally presented concentric annular arrays of staple drivers (352). Staple drivers (352) are arranged to correspond with the arrangement of staple forming pockets (414) described above. Thus, each staple driver (352) is configured to drive a corresponding staple into a corresponding staple forming pocket (414) when stapling head assembly (300) is actuated. Staple driver member (350) also defines a bore (354) that is configured to coaxially receive core member (312) of tubular casing (310).

A cylindraceous knife member (340) is coaxially positioned within staple driver member (350). Knife member (340) includes a distally presented, sharp circular cutting edge (342). Knife member (340) is sized such that knife member (340) defines an outer diameter that is smaller than the diameter defined by the inner annular array of staple drivers (352). Knife member (340) also defines an opening (344) that is configured to coaxially receive core member (312) of tubular casing (310).

A deck member (320) is fixedly secured to tubular casing (310). Deck member (320) includes a distally presented deck surface (322) defining two concentric annular arrays of staple openings (324). Staple openings (324) are arranged to correspond with the arrangement of staple drivers (352) and staple forming pockets (414) described above. Thus, each staple opening (324) is configured to provide a path for a corresponding staple driver (352) to drive a corresponding staple through deck member (320) and into a corresponding staple forming pocket (414) of anvil (400) when stapling head assembly (300) is actuated. The arrangement of staple openings (322) may be modified just like the arrangement of staple forming pockets (414) as described above. It should also be understood that various structures and techniques may be used to contain staples within stapling head assembly (300) before stapling head assembly (300) is actuated.

Deck member (320) defines an inner diameter that is just slightly larger than the outer diameter defined by knife member (340). Deck member (320) is thus configured to allow knife member (340) to translate distally to a point where cutting edge (342) is distal to deck surface (322). By way of example only, deck member (320) may be constructed and operable in accordance with at least some of the teachings of U.S. patent application Ser. No. 15/350,513, entitled "Circular Surgical Stapler with Recessed Deck," filed Nov. 14, 2016, published as U.S. Pub. No. 2018/0132853 on May 17, 2018, the disclosure of which is incorporated by reference herein. Other suitable configurations that may be used for deck member (320) will be apparent to those of ordinary skill in the art in view of the teachings herein.

Figure 6:
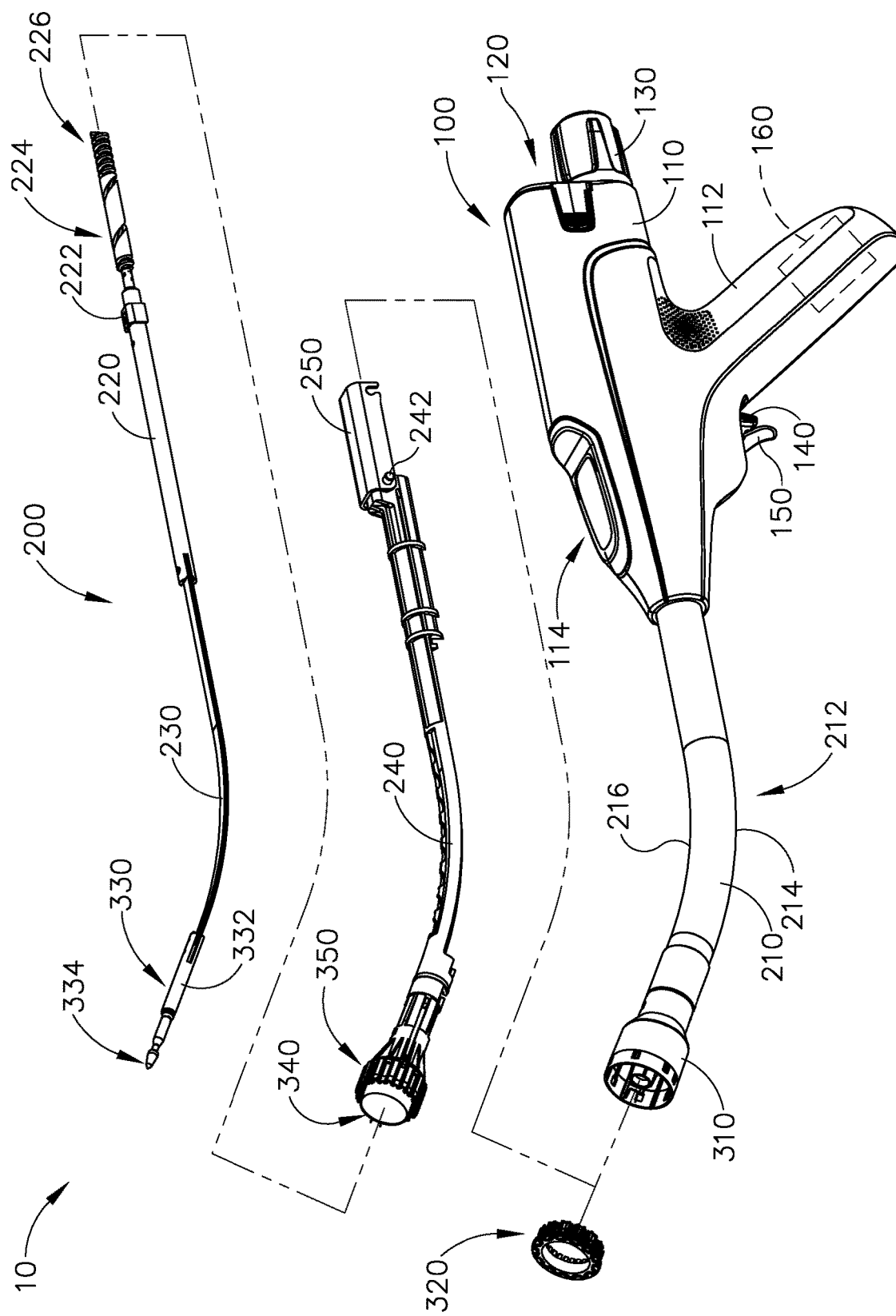
FIG. 6 depicts an exploded perspective view of the circular stapler of FIG. 1, with portions of the shaft assembly shown separately from each other.

FIG. 6 shows various components of shaft assembly (200), which extends distally from handle assembly (100) and couples components of stapling head assembly (300) with components of handle assembly (100). In particular, and as noted above, shaft assembly (200) includes an outer sheath (210) that extends between handle assembly (100) and tubular casing (310). In the present example, outer sheath (210) is rigid and includes a preformed curved section (212) that is configured to facilitate positioning of stapling head assembly (300) within a patient's colon as described below. Curved section (212) includes an inner curve (216) and an outer curve (214).

Shaft assembly (200) further includes a trocar actuation rod (220) and a trocar actuation band assembly (230). The distal end of trocar actuation band assembly (230) is fixedly secured to the proximal end of trocar shaft (332). The proximal end of trocar actuation band assembly (230) is fixedly secured to the distal end of trocar actuation rod (220), such that trocar (330) will translate longitudinally relative to outer sheath (210) in response to translation of trocar actuation band assembly (230) and trocar actuation rod (220) relative to outer sheath (210). Trocar actuation band assembly (230) is configured to flex such that trocar actuation band assembly (230) may follow along the preformed curve in shaft assembly (200) as trocar actuation band assembly (230) is translated longitudinally relative to outer sheath (210). However, trocar actuation band assembly (230) has sufficient column strength and tensile strength to transfer distal and proximal forces from trocar actuation rod (220) to trocar shaft (332). Trocar actuation rod (220) is rigid. A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a coarse helical threading (224) and a fine helical threading (226), which are configured to interact with a nut (132) and knob (130) as described in greater detail below.

Shaft assembly (200) further includes a stapling head assembly driver (240) that is slidably received within outer sheath (210). The distal end of stapling head assembly driver (240) is fixedly secured to the proximal end of staple driver member (350). The proximal end of stapling head assembly driver (240) is secured to a drive bracket (250) via a pin (242). It should therefore be understood that staple driver member (350) will translate longitudinally relative to outer sheath (210) in response to translation of stapling head assembly driver (240) and drive bracket (250) relative to outer sheath (210). Stapling head assembly driver (240) is configured to flex such that stapling head assembly driver (240) may follow along the preformed curve in shaft assembly (200) as stapling head assembly driver (240) is translated longitudinally relative to outer sheath (210). However, stapling head assembly driver (240) has sufficient column strength to transfer distal forces from drive bracket (250) to staple driver member (350).

Figure 7:
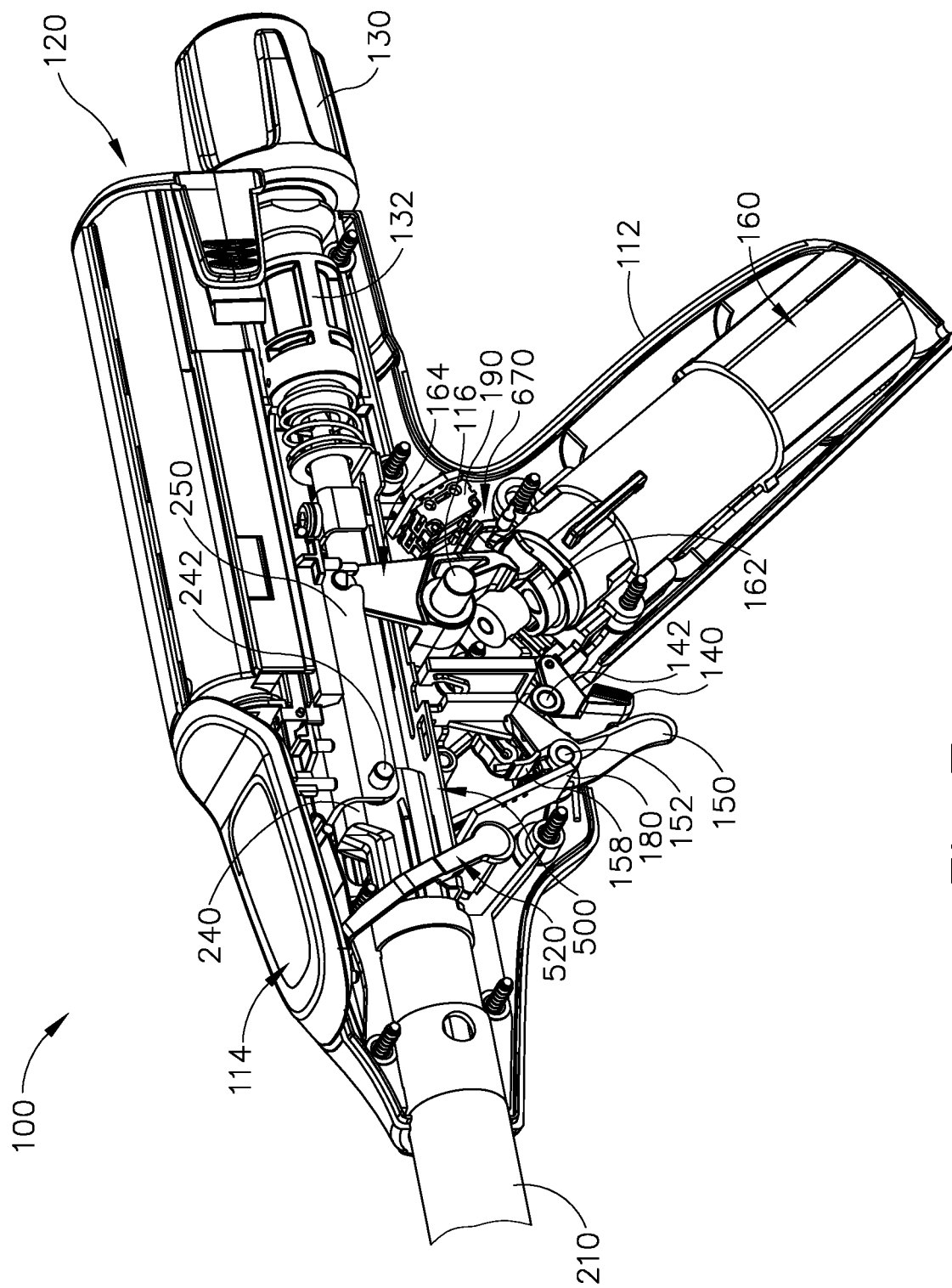
FIG. 7 depicts a perspective view of the handle assembly of the circular stapler of FIG. 1, with a housing half omitted to reveal internal components of the handle assembly.

As shown in FIG. 7, motor (160) is coupled with drive bracket (250) via a cam member (162) and a pivoting arm (164). Pivoting arm (164) is pivotably coupled with housing (166) of handle assembly (100) via a pin (116). Motor (160) is operable to rotate cam member (162). Cam member (162) is configured to drive pivotal movement of pivoting arm (164) when cam member (162) rotates in response to activation of motor. Pivoting arm (164) is configured to drive translation of drive bracket (250) when pivoting arm (164) pivots about pin (116) in response to rotation of cam member (162). Motor (160) is thus operable to drive stapling head assembly driver (240) via cam member (162), pivoting arm (164), and drive bracket (250). By way of example only, these components may be configured and operable in accordance with at least some of the teachings of U.S. Pub. No. 2014/0166717, entitled "Circular Stapler with Selectable Motorized and Manual Control, Including a Control Ring," published Jun. 19, 2014, issued as U.S. Pat. No. 9,532,783 on Jan. 3, 2017, the disclosure of which is incorporated by reference herein.

Figure 12A:
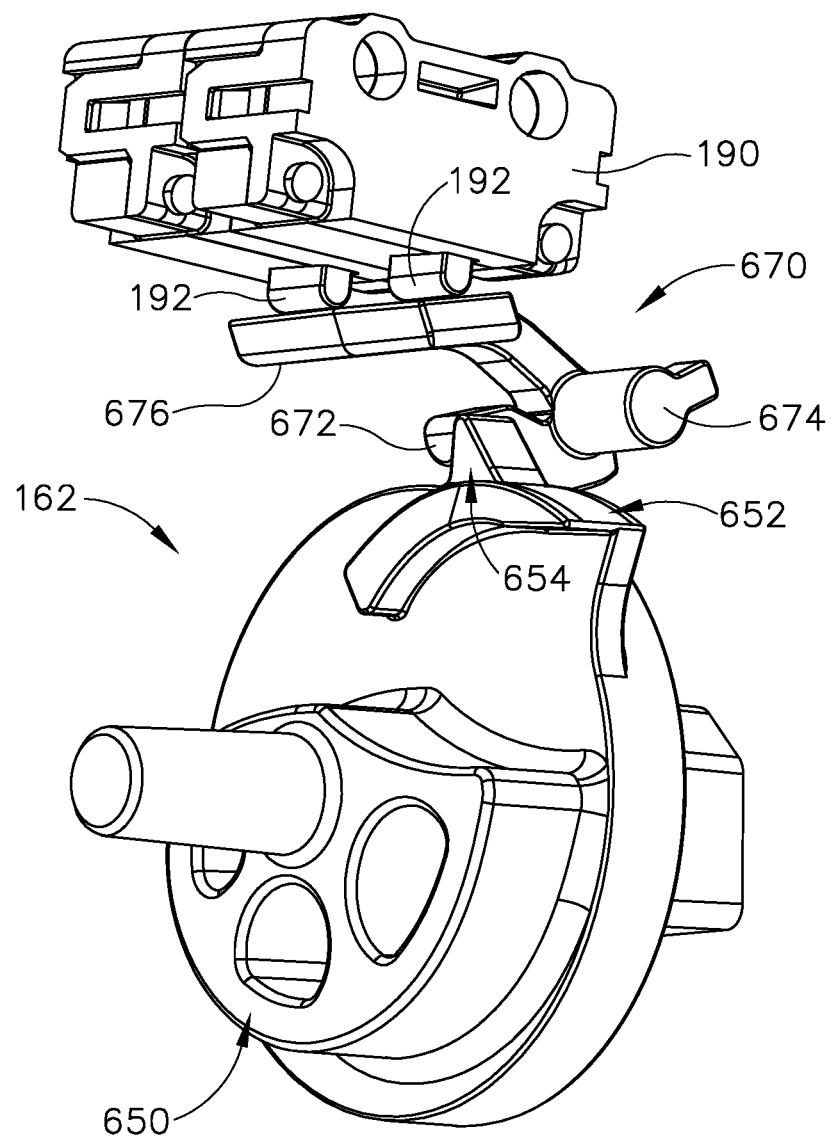
FIG. 12A depicts a perspective view of a rotary cam, a rocker member, and a stop switch of the handle assembly of FIG. 7, with the rotary cam in a first angular position and the rocker member in a first pivotal position.
Figure 12B:
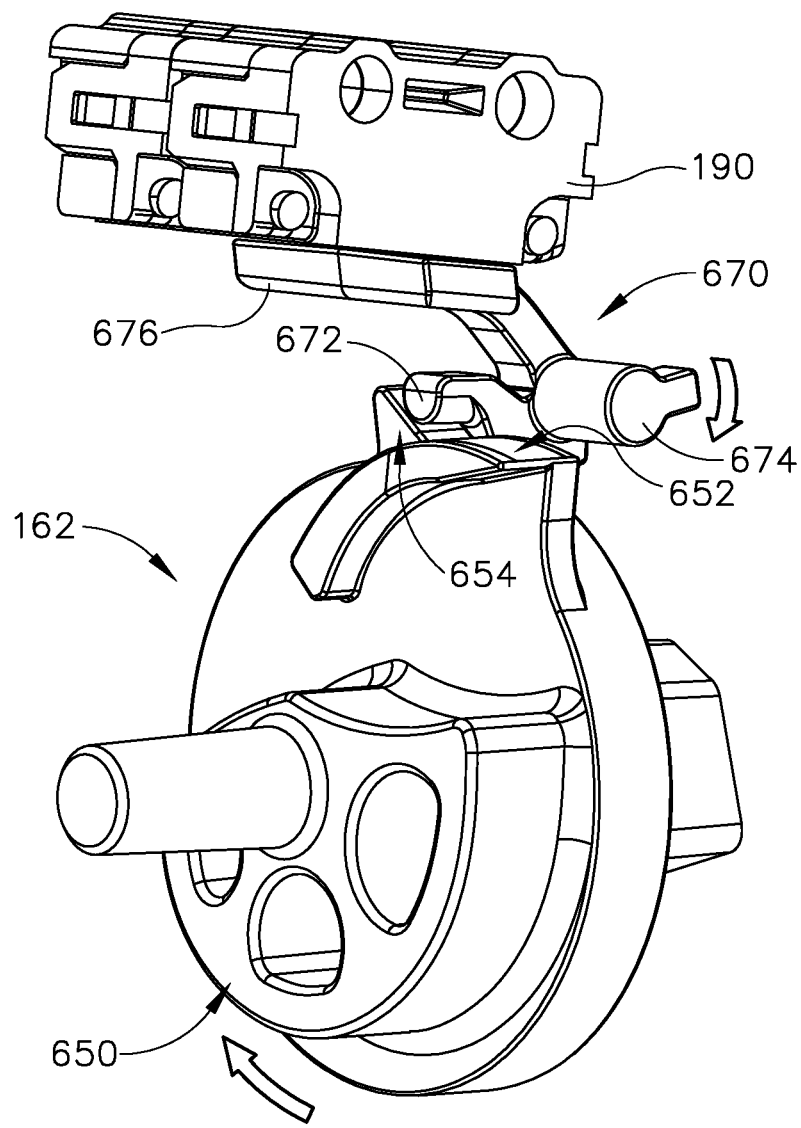
FIG. 12B depicts a perspective view of the rotary cam, rocker member, and stop switch of FIG. 12A, with the rotary cam in a second angular position and the rocker member in a second pivotal position.

In the present example, and as best seen in FIGS. 12A-12B, cam member (162) of the present example has a first cam feature (650), a second cam feature (652), and a third cam feature (654). First cam feature (650) and pivoting arm (164) are configured to cooperatively drive distal movement of stapling head assembly driver (240) as cam member (162) is rotated by motor (160). Second cam feature (652) and pivoting arm (164) are configured to cooperatively drive proximal movement of stapling head assembly driver (240) via cam member (162) as cam member (162) is rotated by motor (160). In the present example, such distal and proximal driving is carried out by cam member (162) rotating in one single angular direction, such that motor (160) does not need to be reversed to provide distal and proximal movement of stapling head assembly driver (240). Moreover, such distal and proximal driving is carried out by cam member (162) rotating just less than 360 degrees. Third cam feature (654) is operable to interact with a rocker member (670) to actuate a pair of switch buttons (192) at the end of the stapling head assembly (300) actuation stroke, as described in greater detail below. Again, cam features (650, 652, 654) may be configured and operable in accordance with at least some of the teachings of U.S. Pub. No. 2014/0166717, issued as U.S. Pat. No. 9,532,783 on Jan. 3, 2017, the disclosure of which is incorporated by reference herein.

B. Exemplary User Interface Features of Circular Stapling Instrument

As shown in FIGS. 1 and 7, handle assembly (100) includes a pistol grip (112) and several components that are operable to actuate anvil (400) and stapling head assembly (300). In particular, handle assembly (100) includes knob (130), a safety trigger (140) a firing trigger (150), a motor (160), and a motor activation module (180). Knob (130) is coupled with trocar actuation rod (220) via a nut (132) (shown in FIG. 7), such that coarse helical threading (224) will selectively engage a thread engagement feature within the interior of the nut; and such that fine helical threading (226) will selectively engage a thread engagement feature within the interior of knob (130). These complementary structures are configured such that trocar actuation rod (220) will first translate proximally at a relatively slow rate, then translate proximally at a relatively fast rate, in response to rotation of knob (130).

Battery pack (120) is operable to provide electrical power to a motor (160) as noted above. Battery pack (120) may be removably coupled with handle assembly (100) through a snap fit or in any other suitable fashion. Battery pack (120) and handle assembly (100) may have complementary electrical contacts, pins and sockets, and/or other features that provide paths for electrical communication from battery pack (120) to electrically powered components in handle assembly (100) when battery pack (120) is coupled with handle assembly (100). It should also be understood that, in some versions, battery pack (120) is unitarily incorporated within handle assembly (100) such that battery back (120) cannot be removed from handle assembly (100).

When anvil (400) is coupled with trocar (330), rotation of knob (130) will provide corresponding translation of anvil relative to stapling head assembly (300). It should also be understood that knob (130) may be rotated in a first angular direction (e.g., clockwise) to retract anvil (400) toward stapling head assembly (300); and in a second angular direction (e.g., counterclockwise) to advance anvil (400) away from stapling head assembly (300). Knob (130) may thus be used to adjust the gap distance between opposing surfaces (412, 322) of anvil (400) and stapling head assembly (300) until a suitable gap distance has been achieved.

Figure 10A:
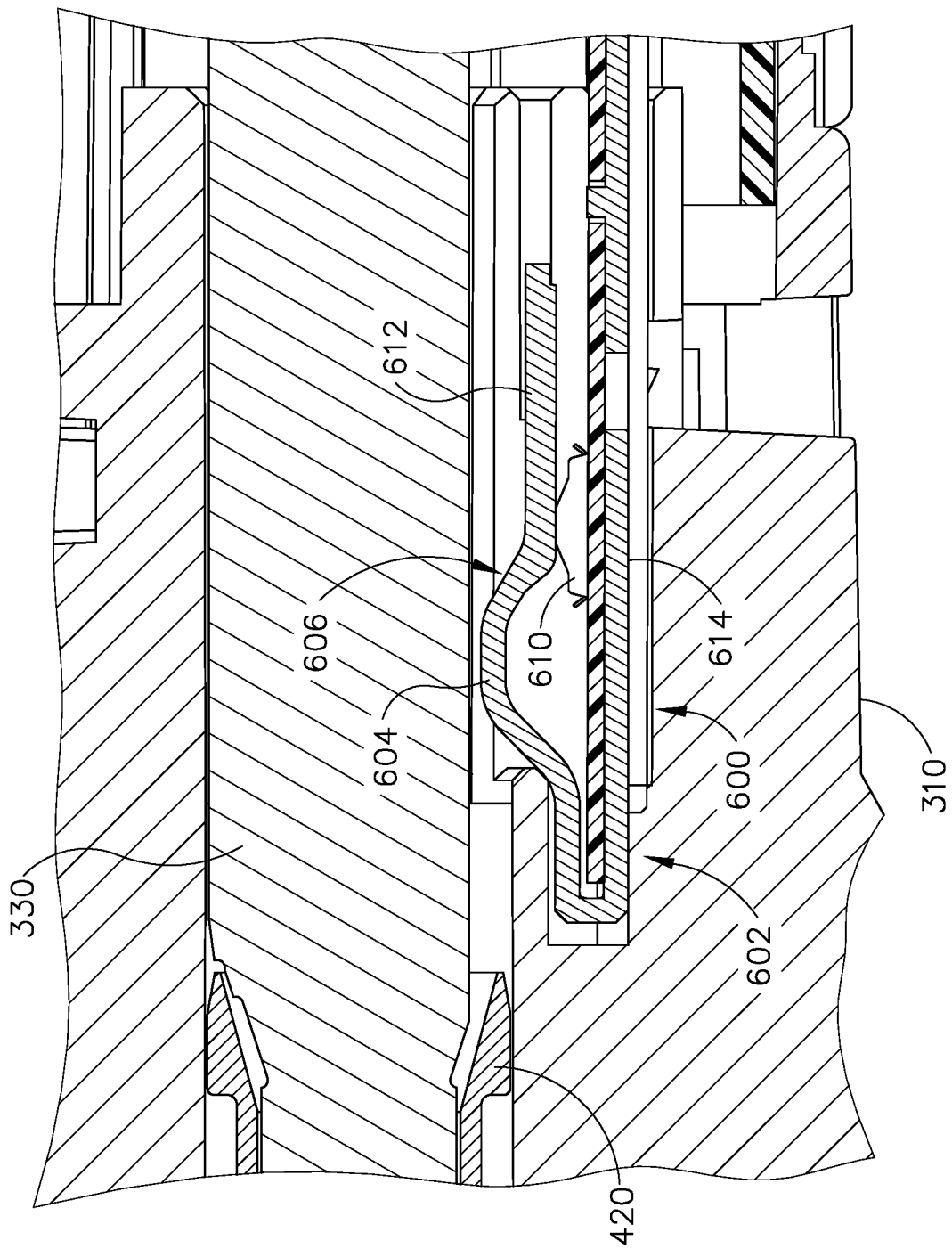
FIG. 10A depicts an enlarged cross-sectional side view of the contact switch of FIG. 9A in the open state of FIG. 9A.

In the present example, handle assembly (100) comprises a user feedback feature (114) that is configured to provide the operator with visual feedback indicating the positioning of anvil (400) in relation to stapling assembly (300). In particular, and as best seen in FIG. 10, user feedback feature (114) of the present example includes a graphical indicator (550), which includes fixed linear indicia (552, 554, 556), graphical representations (560, 562) of staples, and a checkmark graphic (564). User feedback feature (114) further defines a window (570) through which an indicator needle (522) may be viewed. In some variations, user feedback feature (114) further includes a field (566) that may indicate the size of staples in stapling head assembly (300), the size of the gap defined between anvil (400) and stapling head assembly (300), and/or other information.

Figure 8:
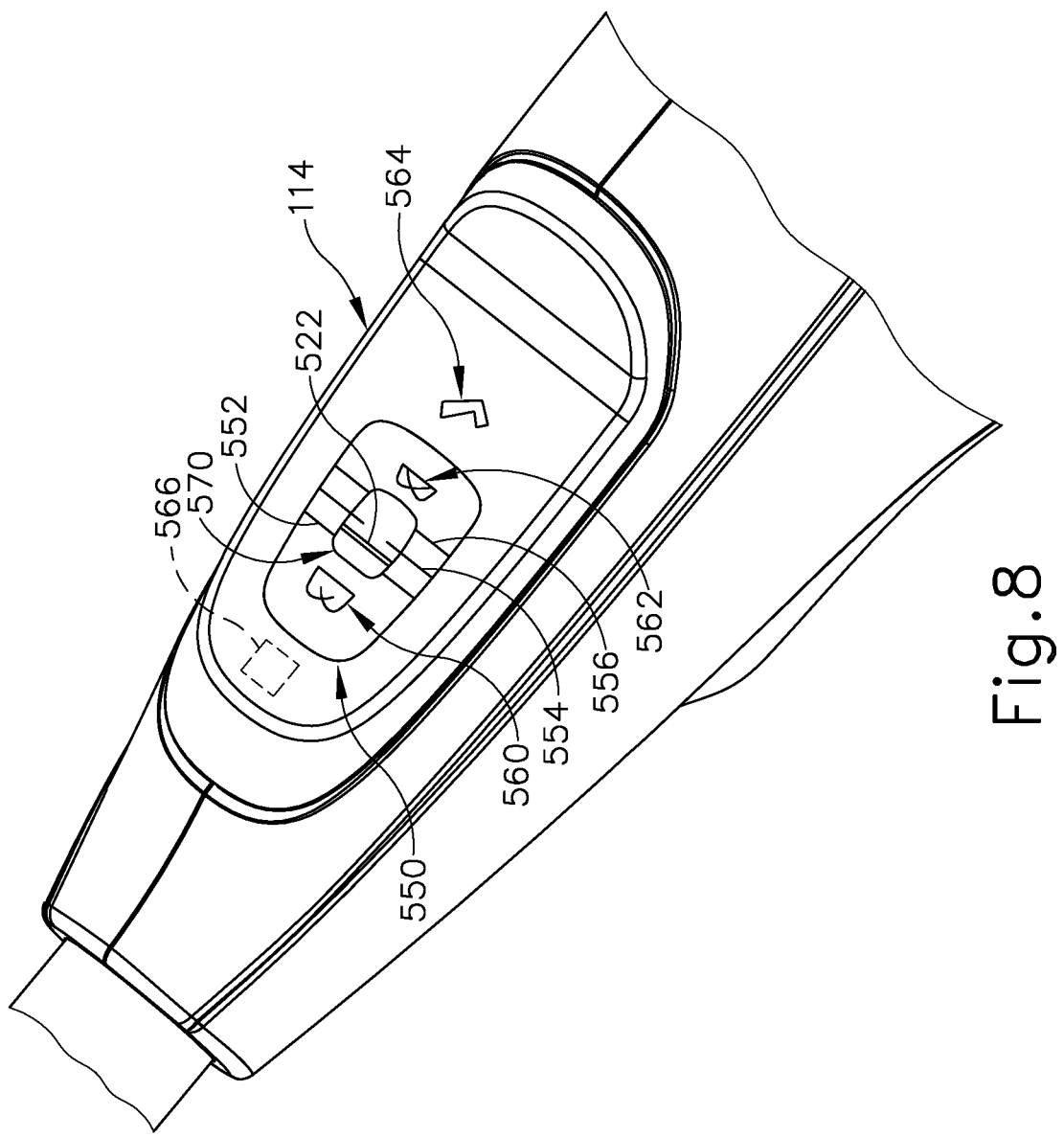
FIG. 8 depicts a perspective view of a user interface of the handle assembly of FIG. 7.

Indicator needle (522) is a feature of indicator member (520), which is shown in FIG. 8. Indicator member (520) is coupled with a bracket (500), which is configured to translate longitudinally based on longitudinal movement of trocar actuation rod (220). When bracket (500) translates longitudinally, indicator member (520) pivots within handle assembly (100). This pivotal movement of indicator member (520) is viewable to the operator as corresponding movement of indicator needle (522) is viewable through window (570). By way of example only, indicator member (520) and bracket (500) may be constructed and operable in accordance with at least some of the teachings of U.S. Pub. No. 2018/0310938, entitled "Hysteresis Removal Feature in Surgical Stapling Instrument," published Nov. 1, 2018, the disclosure of which is incorporated by reference herein. Other suitable ways in which indicator member (520) and bracket (500) may be constructed and operable will be apparent to those of ordinary skill in the art in view of the teachings herein.

As the operator rotates knob (130) to adjust the longitudinal position of anvil (400) relative to stapling head assembly (300), the operator may observe the position of indicator needle (522) through window (570). Initially, indicator needle (522) may be positioned at or near the distal end of window (570). As anvil (400) continues to move proximally, indicator needle (522) will eventually move proximally relative to window (570). The operator may view the position of indicator needle (522) in relation to fixed linear indicia (552, 554, 556). The distal-most and proximal-most indicia (552, 556) may represent the boundaries of a "green zone," which is the acceptable range of distance between anvil (400) and stapling head assembly (300) for successful actuation of stapling head assembly (300). Thus, if indicator needle (522) is distal to distal-most indicia (552), the distance between anvil (400) and stapling head assembly (300) is too large; and if indicator needle (522) is proximal to proximal-most indicia (556), the distance between anvil (400) and stapling head assembly (300) is too small. Indicia (554) is longitudinally positioned between indicia (552, 556). Graphical representation (560) represents a relatively tall formed staple (e.g., suitable for use in relatively thick tissue); while graphical representation (562) represents a relatively short formed staple (e.g., suitable for use in relatively thin tissue). Graphical representations (560, 562) may thus facilitate the operator's decision, based on tissue observations or otherwise, on whether and how to achieve a desired formed staple height by selecting an appropriate corresponding spatial relationship between indicator needle (522) and indicia (552, 554, 556).

In the present example, window (570) is illuminated via a light emitting diode (LED) (702), further facilitating viewing of indicator needle (522) in window (570). In addition, checkmark graphic (564) is illuminated via another LED (704) when stapling head assembly (300) completes a stapling and cutting cycle. In the present example, the illumination of LED (704) is triggered by actuation of switch buttons (192), which are described in greater detail below as being actuated at the end of a stapling and cutting cycle. Thus, the operator may further rely on illumination of checkmark graphic (564) to verify that it is safe to advance anvil (400) distally away from the anastomosis (70) and remove instrument (10) from the patient. By way of example only, LED (702) may be configured to emit white visible light while LED (704) may be configured to emit green visible light. An exemplary way in which LEDs (702, 704) may be integrated into a control circuit (700) will be described in greater detail below with reference to FIG. 14. Other examples will be apparent to those of ordinary skill in the art in view of the teachings herein.

C. Exemplary Anvil Attachment Sensor

In some versions of instrument (10) it may desirable to provide instrument (10) with features that are configured to indicate proper and/or improper attachment of anvil (400) to trocar (330) of stapling head assembly (300). For instance, features may be configured to prevent firing of stapling head assembly (300) unless anvil (400) is properly attached to trocar (330). If anvil (400) is properly attached to trocar (330), firing of stapling head assembly (300) may be enabled. FIGS. 9A-10B depict an exemplary switch assembly (600) that is incorporated into stapling head assembly (300) in the present example. Switch assembly (600) includes a dome switch (610) and a resilient actuator spring (602). Actuator spring (602) is secured within a cavity (606) formed within tubular casing (310). Dome switch (610) is positioned between a pair of flanges (612, 614) of actuator spring (602) such that movement of flange (612) toward flange (614) will actuate dome switch (610).

When anvil (400) is properly secured to trocar (330) and is retracted proximally as described herein, anvil (400) causes movement of flange (612) toward flange (614) so as to actuate dome switch (610). Actuation of dome switch (610) may provide audible, tactile, and/or visible feedback to an operator indicating proper attachment. Various suitable features that may be used to provide such a response to actuation of dome switch (610) will be apparent to those of ordinary skill in the art in view of the teachings herein. In addition, in the present example actuation of dome switch (610) may enables firing of stapling head assembly (300). In other words, unless dome switch (610) has been actuated, stapling head assembly (300) may not be fired in the present example.

Figure 9A:
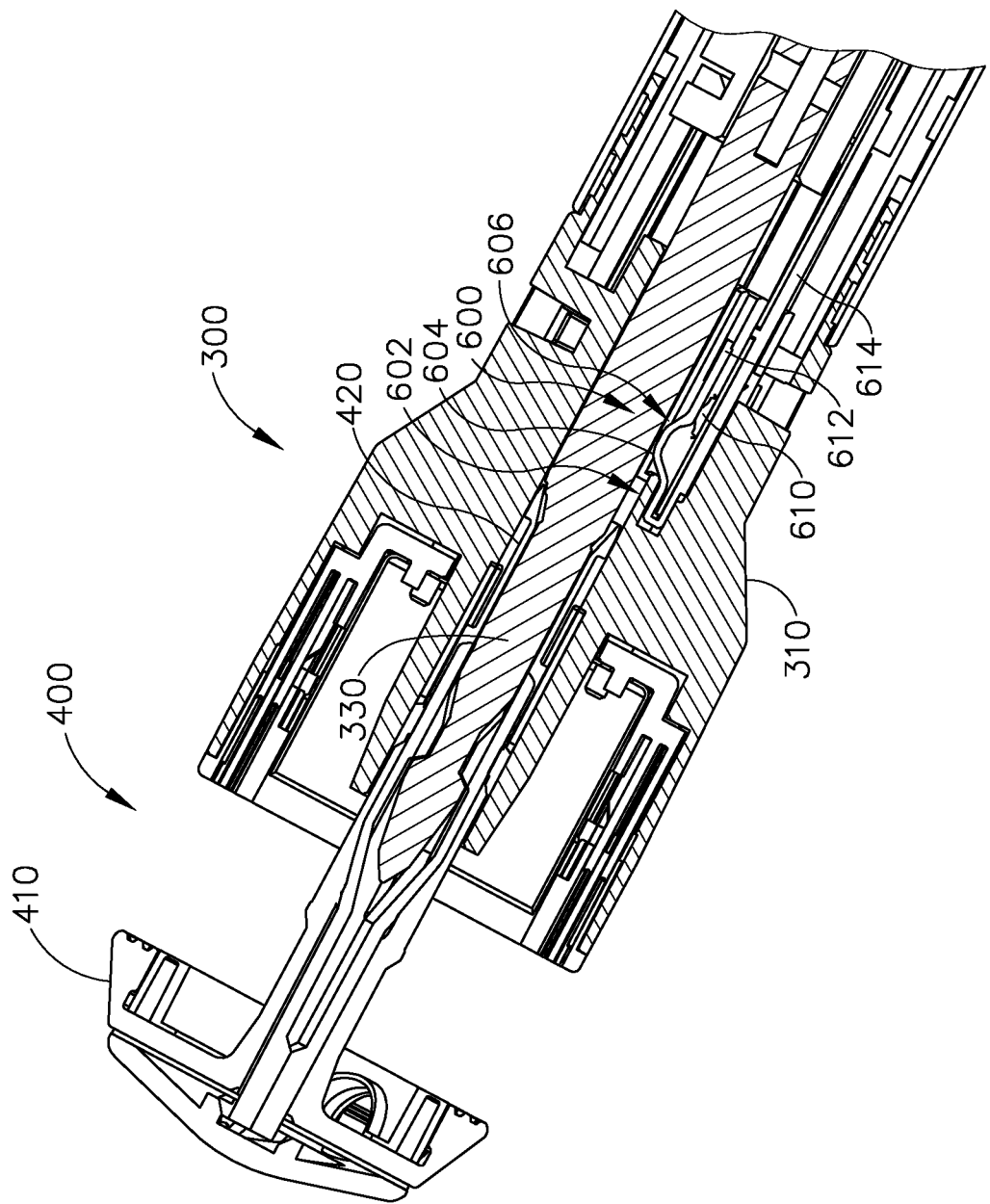
FIG. 9A depicts a cross-sectional side view of the distal end of the circular stapler of FIG. 1, with a contact switch of the circular stapler in an open state.
Figure 9B:
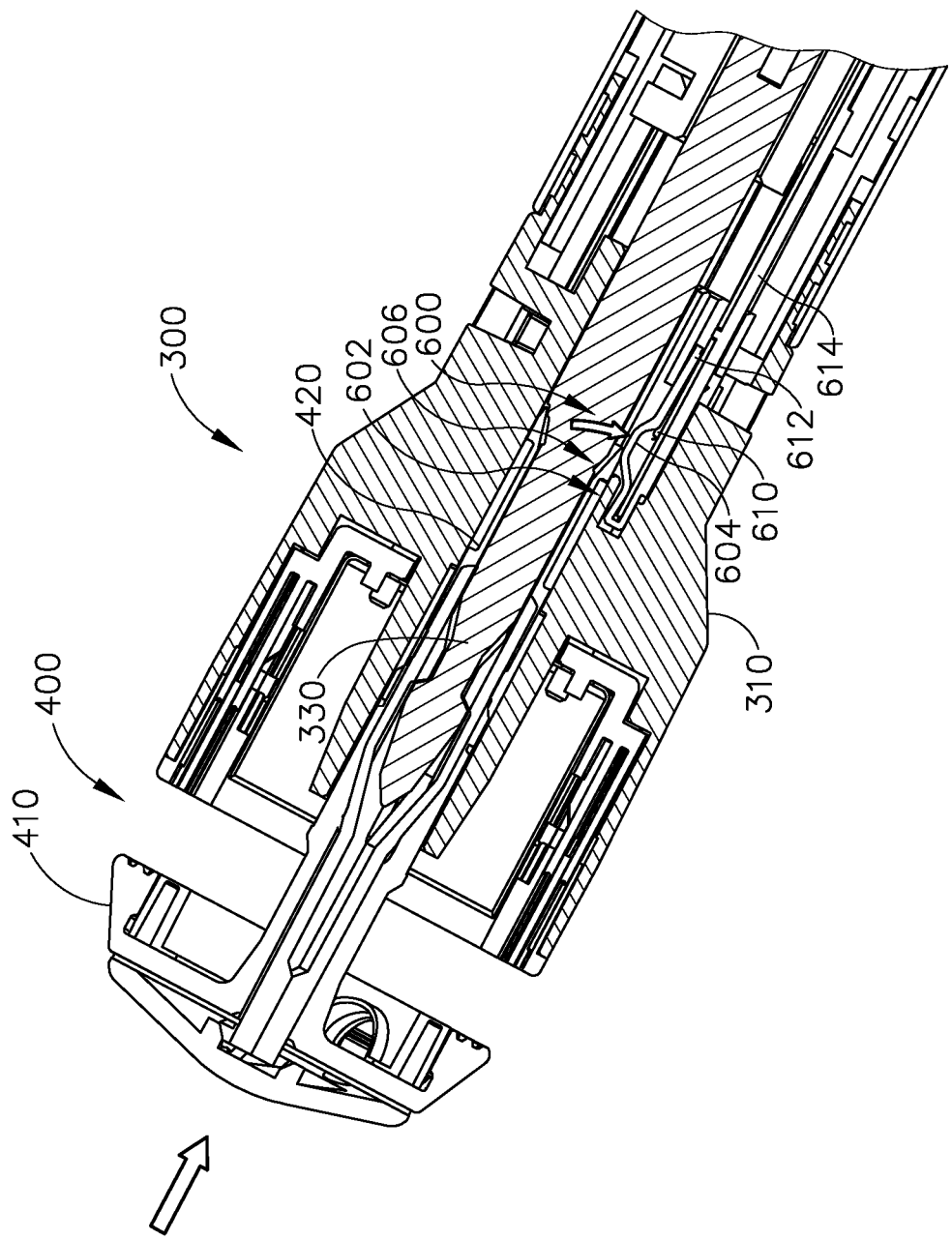
FIG. 9B depicts a cross-sectional side view of the distal end of the circular stapler of FIG. 1, with the contact switch of FIG. 9A moved into a closed state by proximal translation of a trocar and an anvil of the circular stapler.
Figure 10B:
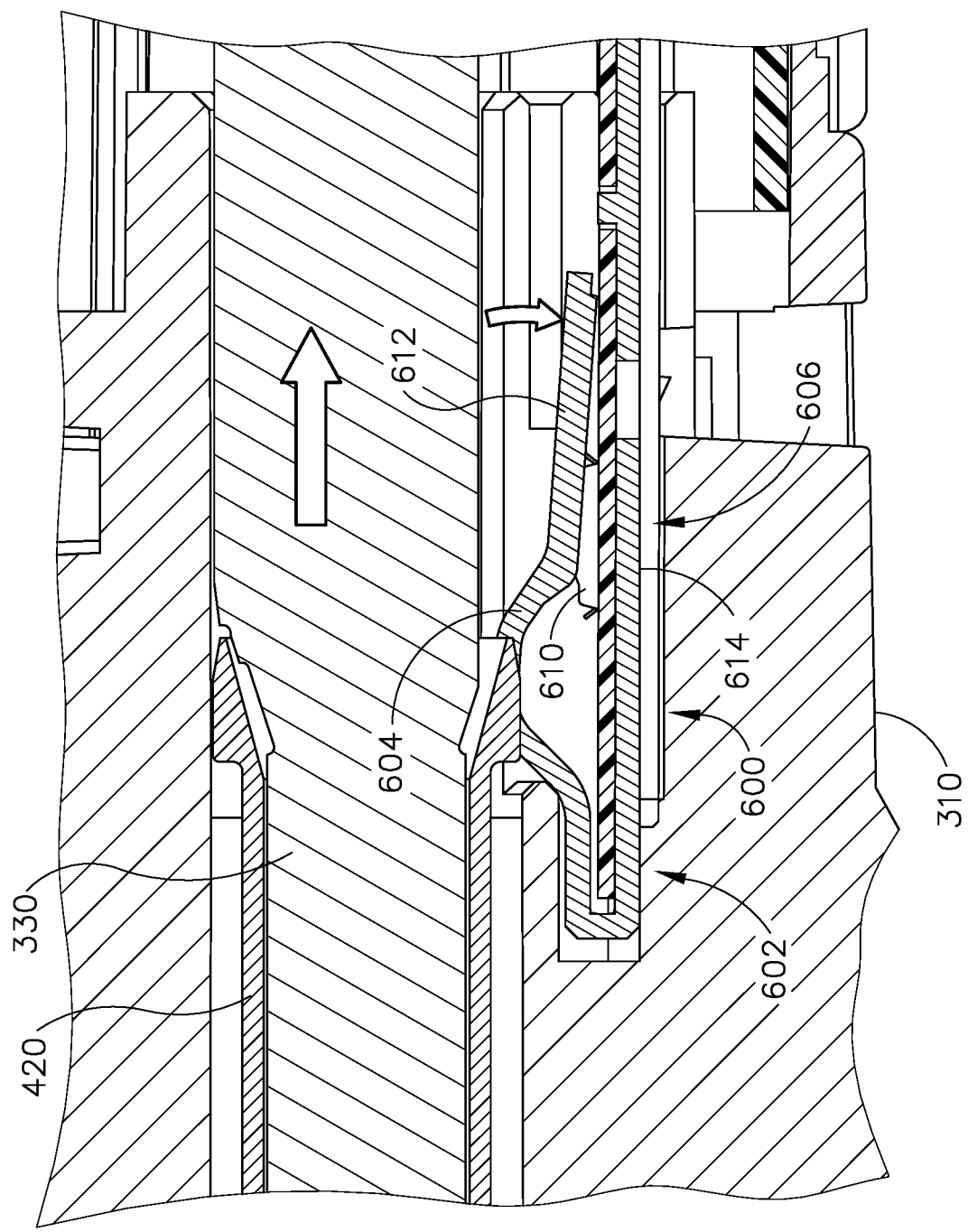
FIG. 10B depicts an enlarged cross-sectional side view of the contact switch of FIG. 9A moved into the closed state of FIG. 9B by proximal translation of the trocar and the anvil of the circular stapler.

After anvil (400) is secured to trocar (330), the operator then rotates knob (130) to cause trocar (330) and anvil (400) to retract proximally as described above. When trocar (330) and anvil (400) are properly secured to one another, this proximal retraction of trocar (330) and anvil (400) compresses the tissue of tubular anatomical structures (20, 40) between surfaces (412, 322) of anvil (400) and stapling head assembly (300) as described below with reference to FIGS. 13A-13E. When trocar (330) and anvil (400) are not properly secured to one another, trocar (330) is retracted proximally without anvil (400), such that the tissue of tubular anatomical structures (20, 40) remains uncompressed. When trocar (330) and anvil (400) are properly secured to one another, as trocar (330) and anvil (400) are retracted proximally, a proximal end of shank (420) of anvil (400) engages a raised portion (604) of flange (612) of actuator spring (602) and thereby drives flange (612) toward flange (614), thereby actuating dome switch (610) as shown in FIGS. 9B and 10B. As mentioned above, such actuation of dome switch (610) may provide audible, tactile, and/or visible feedback to an operator indicating proper attachment. Moreover, such actuation of dome switch (610) enables firing of stapling head assembly (300). In other words, unless dome switch (610) has been actuated, stapling head assembly (300) may not be fired. An exemplary way in which dome switch (610) may be integrated into a control circuit (700) will be described in greater detail below with reference to FIG. 14. Other examples will be apparent to those of ordinary skill in the art in view of the teachings herein.

D. Exemplary Firing Circuit Activation and De-Activation Features

Firing trigger (150) is operable to activate motor (160) to thereby actuate stapling head assembly (300). Safety trigger (140) is operable to selectively block actuation of firing trigger (150) based on the longitudinal position of anvil (400) in relation to stapling head assembly (300). Firing trigger (150) may thus not be actuated until after safety trigger (140) has been actuated. Handle assembly (100) also includes components that are operable to selectively lock out both triggers (140, 150) based on the position of anvil (400) relative to stapling head assembly (300). When triggers (140, 150) are locked out, safety trigger (140) is prevented from moving to permit actuation of firing trigger (150), and firing trigger (150) is prevented from initiating actuation of stapling head assembly (300). Thus, trigger (150) is only operable to initiate actuation of stapling head assembly (300) when the position of anvil (400) relative to stapling head assembly (300) is within a predefined range. By way of example only, such lockout features may be constructed and operable in accordance with at least some of the teachings of U.S. Pub. No. 2016/0374667, entitled "Surgical Stapler with Anvil Seating Detection," published Dec. 29, 2016, issued as U.S. Pat. No. 10,307,157 on Jun. 4, 2019, the disclosure of which is incorporated by reference herein.

Figure 11B:
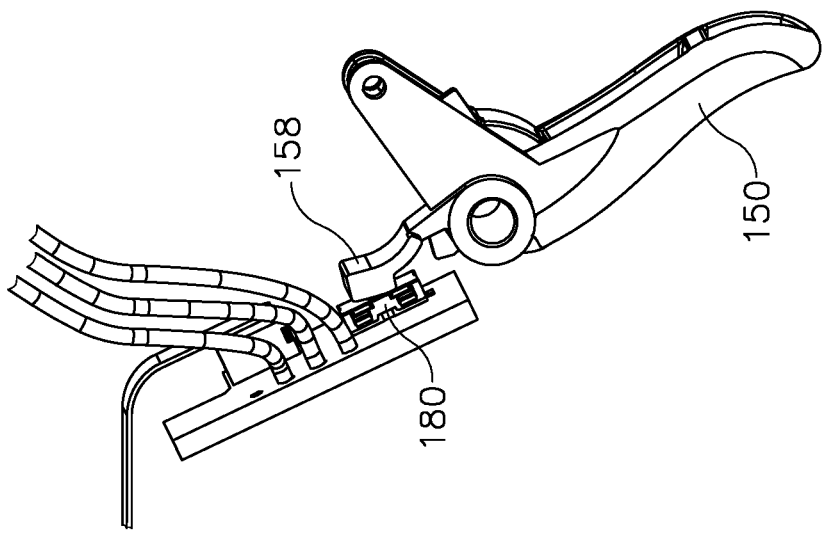
FIG. 11B depicts a perspective view of the firing trigger and motor activation module of FIG. 11A, with the firing trigger in an actuated position.
Figure 11A:
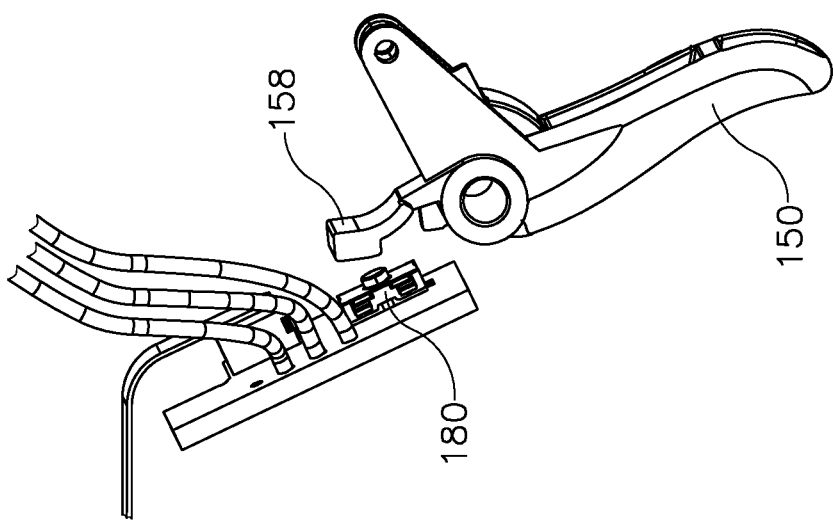
FIG. 11A depicts a perspective view of a firing trigger and motor activation module of the handle assembly of FIG. 7, with the firing trigger in a non-actuated position.

As best seen in FIGS. 11A-11B firing trigger (150) of the present example includes an integral actuation paddle (158). In scenarios when safety trigger (140) has been actuated to permit actuation of firing trigger (150), paddle (158) pivots forwardly as firing trigger (150) pivots from the position shown in FIG. 11A to the position shown in FIG. 11B. Paddle (158) is configured to actuate a switch (182) (see FIG. 14) of a motor activation module (180) when firing trigger (150) pivots from the position shown in FIG. 11A to the position shown in FIG. 11B. Switch (182) of motor activation module (180) is in communication with battery pack (120) and motor (160), such that motor activation module (180) is configured to provide activation of motor (160) with electrical power from battery pack (120) in response to paddle (158) actuating switch (182) of motor activation module (180). Thus, motor (160) will be activated when firing trigger (150) is pivoted from the position shown in FIG. 11A to the position shown in FIG. 11B. This activation of motor (160) will actuate stapling head assembly (300) as described herein. By way of example only, this actuation may be carried out in accordance with at least some of the teachings of U.S. Pub. No. 2016/0374666, entitled "Surgical Stapler with Reversible Motor," published Dec. 29, 2016, issued as U.S. Pat. No. 10,456,134 on Oct. 29, 2019, the disclosure of which is incorporated by reference herein. An exemplary way in which motor activation module (180) may be integrated into a control circuit (700) will be described in greater detail below with reference to FIG. 14. Other examples will be apparent to those of ordinary skill in the art in view of the teachings herein.

As noted above, a third cam feature (654) of cam member (162) is configured to interact with a rocker member (670) to actuate a pair of switch buttons (192) at the end of the stapling head assembly (300) actuation stroke. FIG. 12A shows cam member (162) at the beginning of the actuation stroke; while FIG. 12B shows cam member (162) at the end of the actuation stroke. As shown in FIG. 12B, rocker member (670) comprises a bearing member (672), an integral pin (674), and a paddle (676). At the stage shown in FIG. 12A, rocker member (670) is in a first angular position, such that switch buttons (192) are in a non-actuated state. At the stage shown in FIG. 12B, third cam feature (654) has engaged bearing member (672), thereby driving rocker member (670) to pivot about the axis of pin (674). As rocker member (670) has pivoted to the position shown in FIG. 12B, paddle (676) actuates switch buttons (192). Switch buttons (192) are a feature of motor stop module (190), which is configured to prevent motor (160) from further activation when switch buttons (192) have been actuated. An exemplary way in which motor stop module (190) may be integrated into a control circuit (700) will be described in greater detail below with reference to FIG. 14. Other examples will be apparent to those of ordinary skill in the art in view of the teachings herein.

In the present example, motor stop module (190) reverses the polarity of electrical power provided to motor (160) when switch buttons (192) are actuated. This results in stopping activation of motor (160) once an actuation stroke of stapling head assembly (300) has been completed. By way of example only, motor stop module (190) may be configured and operable in accordance with at least some of the teachings of U.S. Pub. No. 2015/0083774, issued as U.S. Pat. No. 9,907,552 on Mar. 6, 2018, the disclosure of which is incorporated by reference herein. Other suitable configurations will be apparent to those of ordinary skill in the art in view of the teachings herein.

E. Exemplary Anastomosis Procedure with Circular Stapling Instrument

FIGS. 13A-13E show instrument (10) being used to form an anastomosis (70) between two tubular anatomical structures (20, 40). By way of example only, the tubular anatomical structures (20, 40) may comprise sections of a patient's esophagus, sections of a patient's colon, other sections of the patient's digestive tract, or any other tubular anatomical structures. In some versions, one or more diseased portions of a patient's colon are removed, with the tubular anatomical structures (20, 40) of FIGS. 13A-13E representing the remaining severed portions of the colon.

Figure 13A:
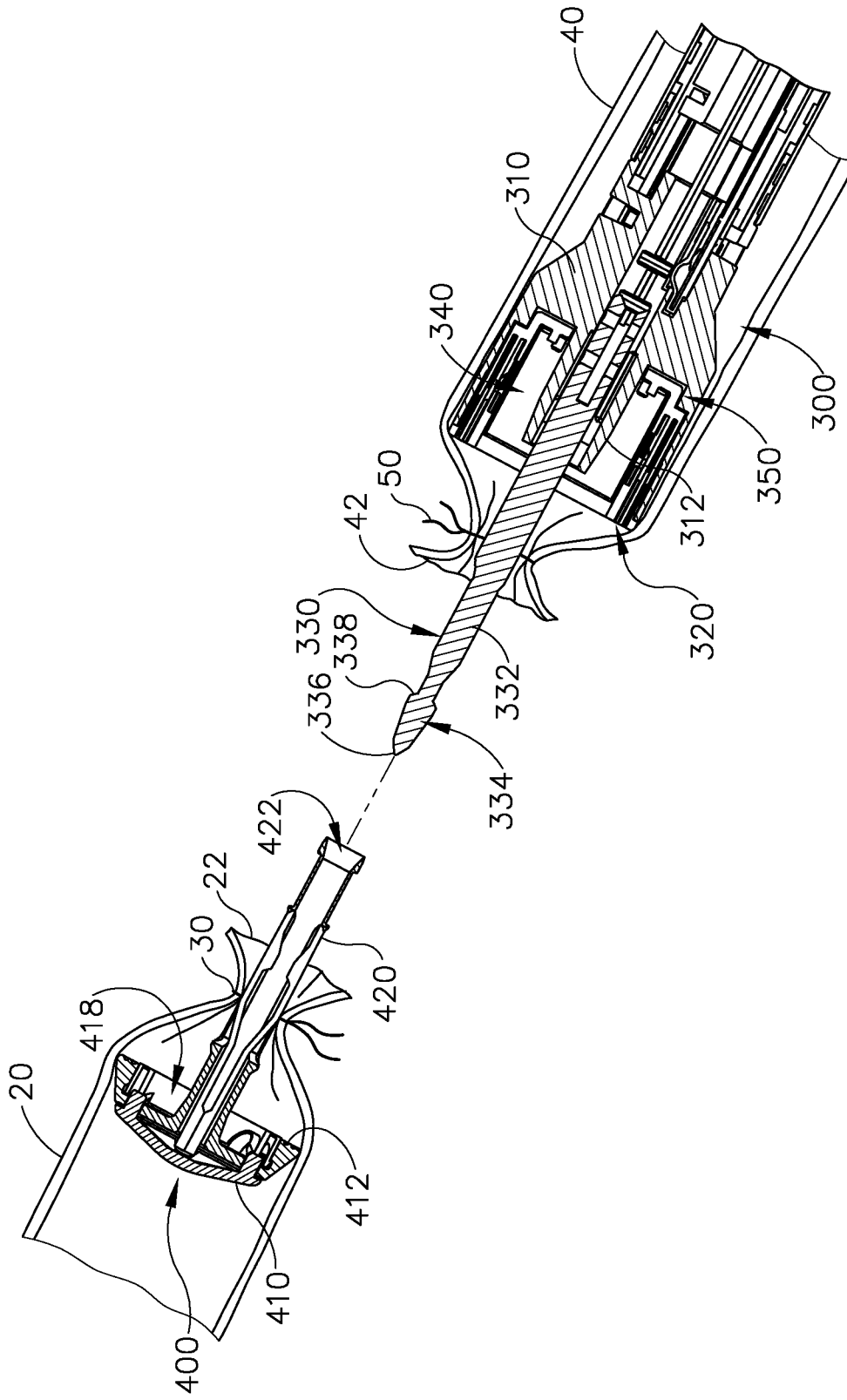
FIG. 13A depicts a cross-sectional side view of the anvil of FIG. 3 positioned within a first section of a digestive tract and the stapling head assembly of FIG. 4 positioned in a second section of the digestive tract, with the anvil separated from the stapling head assembly.

As shown in FIG. 13A, anvil (400) is positioned in one tubular anatomical structure (20) and stapling head assembly (300) is positioned in another tubular anatomical structure (40). In versions where tubular anatomical structures (20, 40) comprise sections of a patient's colon, stapling head assembly (300) may be inserted via the patient's rectum. It should also be understood that the procedure depicted in FIGS. 13A-13E is an open surgical procedure, though the procedure may instead be performed laparoscopically. By way of example only, the surgical procedure may be performed laparoscopically in accordance with at least some of the teachings of U.S. Pub. No. 2016/0100837, entitled "Staple Cartridge," published Apr. 14, 2016, issued as U.S. Pat. No. 10,076,325 on Sep. 18, 2018, the disclosure of which is incorporated by reference herein; and/or U.S. Pub. No. 2017/0086848, entitled "Apparatus and Method for Forming a Staple Line with Trocar Passageway," published Mar. 30, 2017, issued as U.S. Pat. No. 10,485,548 on Nov. 29, 2019, the disclosure of which is incorporated by reference herein. Various other suitable ways in which instrument (10) may be used to form an anastomosis (70) in a laparoscopic procedure will be apparent to those of ordinary skill in the art in view of the teachings herein.

As shown in FIG. 13A, anvil (400) is positioned in tubular anatomical structure (20) such that shank (420) protrudes from the open severed end (22) of tubular anatomical structure (20). A purse-string suture (30) is provided about a mid-region of shank (420) to generally secure the position of anvil (400) in tubular anatomical structure (20). Similarly, stapling head assembly (300) is positioned in tubular anatomical structure (40) such that trocar (330) protrudes from the open severed end (42) of tubular anatomical structure (20). A purse-string suture (50) is provided about a mid-region of shaft (332) to generally secure the position of stapling head assembly (300) in tubular anatomical structure (40).

Figure 13B:
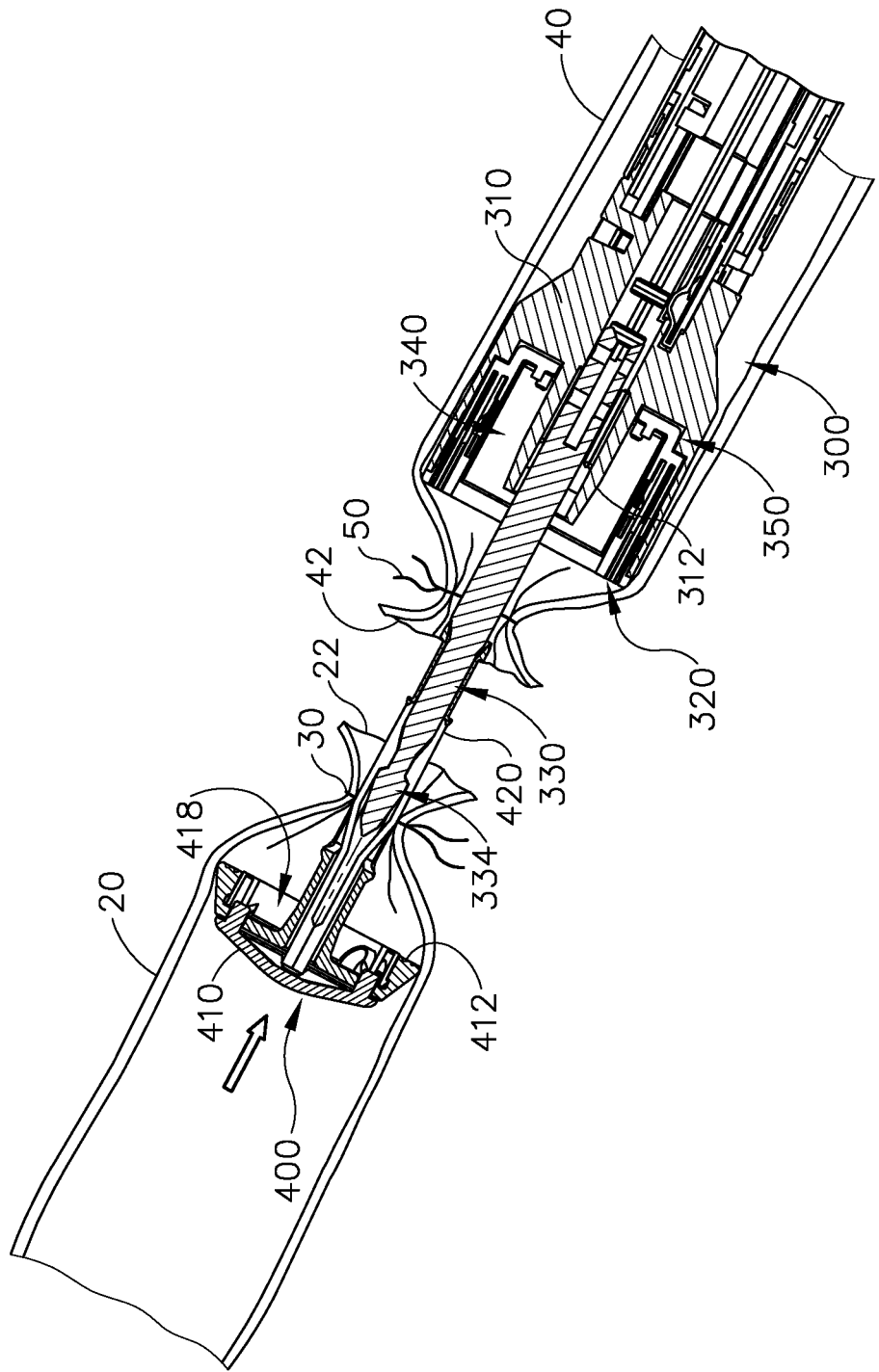
FIG. 13B depicts a cross-sectional side view of the anvil of FIG. 3 positioned within the first section of the digestive tract and the stapling head assembly of FIG. 4 positioned in the second section of the digestive tract, with the anvil secured to the stapling head assembly.

Next, anvil (400) is secured to trocar (330) by inserting trocar (330) into bore (422) as shown in FIG. 13B. Latch members (430) engage head (334) of trocar (330), thereby providing a secure fit between anvil (400) and trocar (330).

Figure 13C:
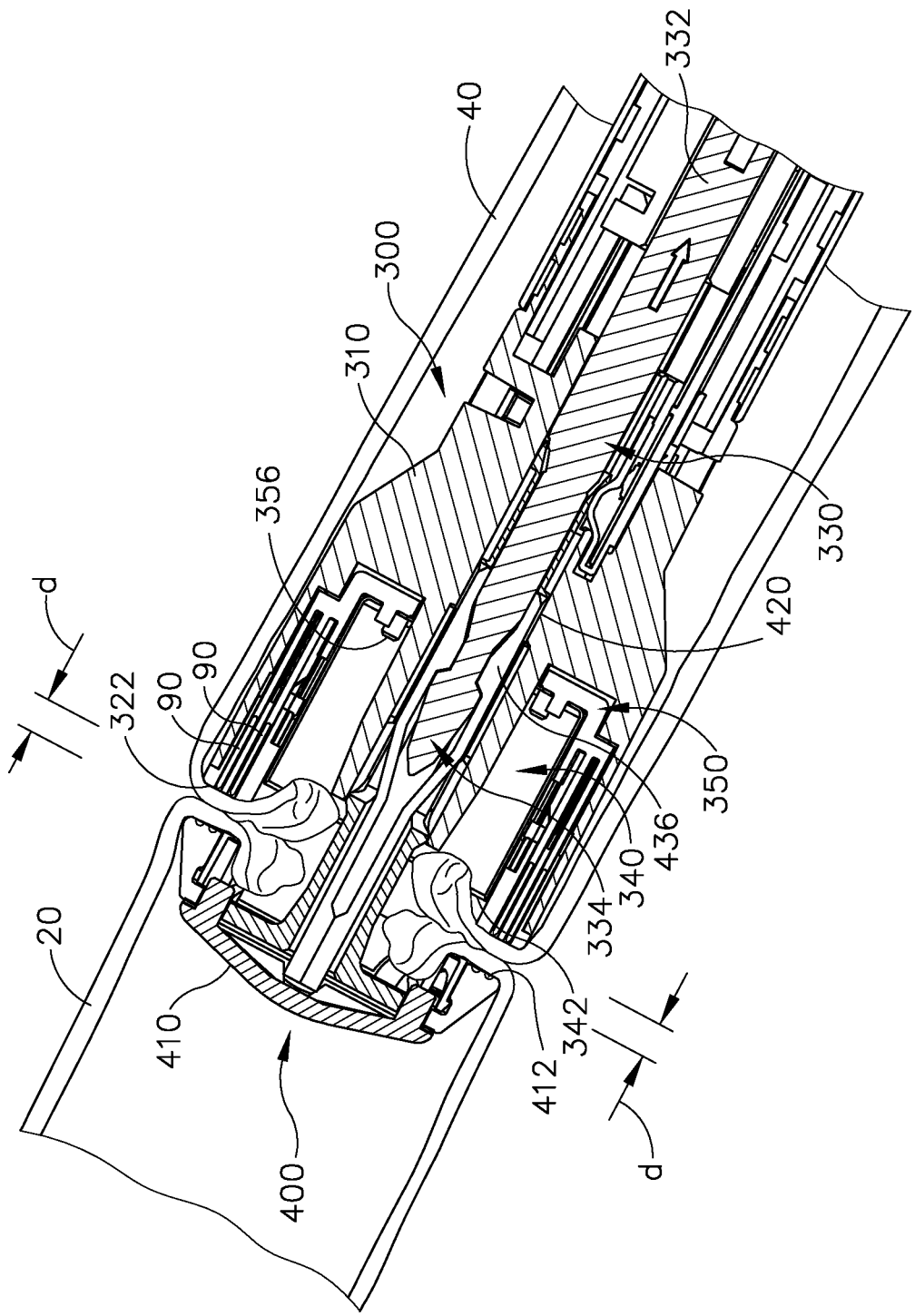
FIG. 13C depicts a cross-sectional side view of the anvil of FIG. 3 positioned within the first section of the digestive tract and the stapling head assembly of FIG. 4 positioned in the second section of the digestive tract, with the anvil retracted toward the stapling head assembly to thereby clamp tissue between the anvil and the stapling head assembly.

The operator then rotates knob (130) while holding handle assembly (100) stationary via pistol grip (112). This rotation of knob (130) causes trocar (330) and anvil (400) to retract proximally, as described above. As shown in FIG. 13C, this proximal retraction of trocar (330) and anvil (400) compresses the tissue of tubular anatomical structures (20, 40) between surfaces (412, 322) of anvil (400) and stapling head assembly (300). The operator observes user feedback feature (114) to determine whether the gap distance (d) between opposing surfaces (412, 322) of anvil (400) and stapling head assembly (300) is appropriate; and makes any necessary adjustments via knob (130).

Figure 13D:
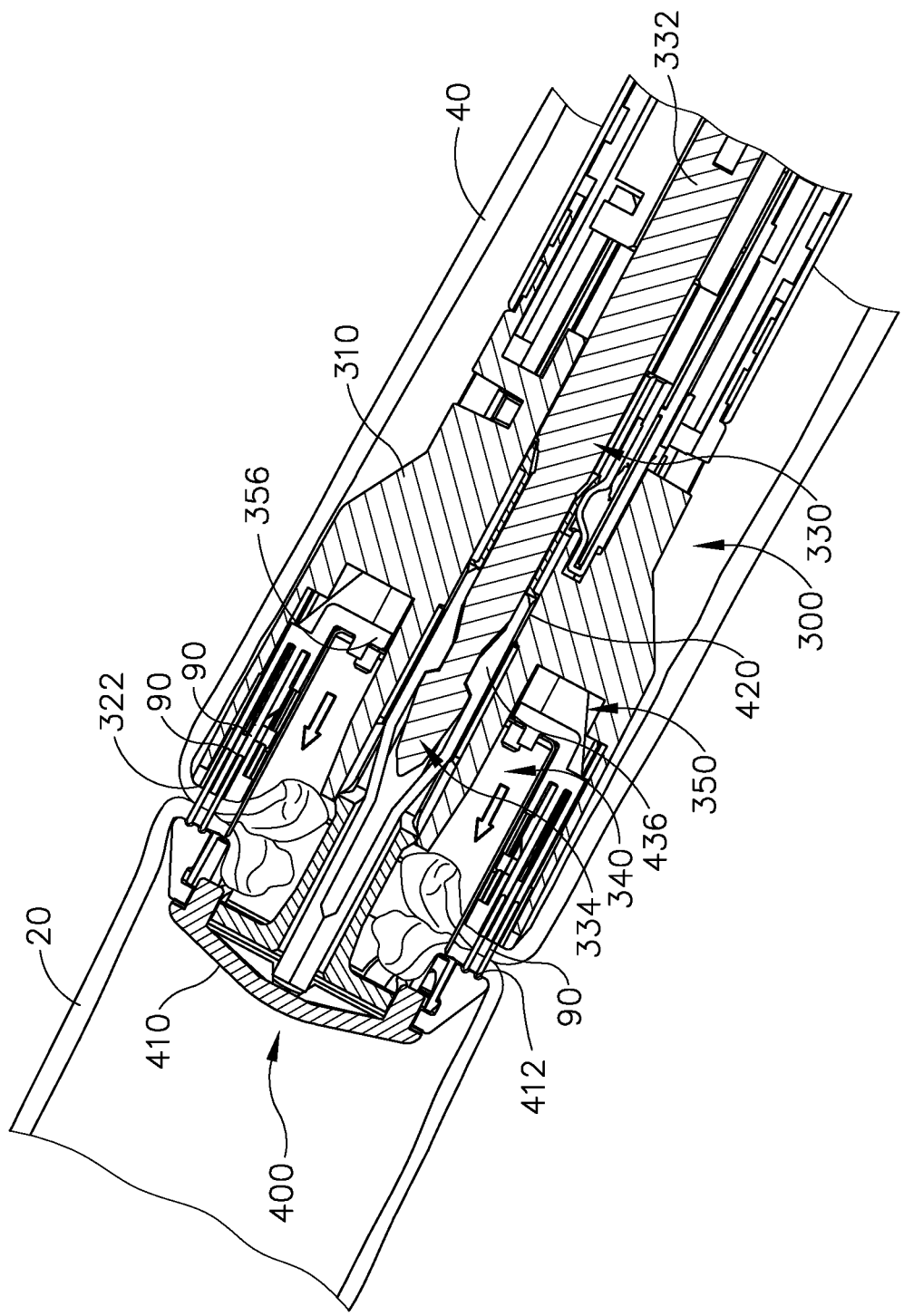
FIG. 13D depicts a cross-sectional side view of the anvil of FIG. 3 positioned within the first section of the digestive tract and the stapling head assembly of FIG. 4 positioned in the second section of the digestive tract, with the stapling head assembly actuated to sever and staple the clamped tissue.

Once the operator has appropriately set the gap distance (d) via knob (130), the operator actuates safety trigger (140) to enable actuation of firing trigger (150). The operator then actuates firing trigger (150). This actuation of firing trigger (150) in turn actuates switch (182) of motor activation module (180), which in turn activates motor (160) to thereby actuate stapling head assembly (300) by driving knife member (340) and staple driver member (350) distally as shown in FIG. 13D. As knife member (340) translates distally, cutting edge (342) of knife member (340) cooperates with inner edge (416) of anvil (400), thereby shearing excess tissue that is positioned within annular recess (418) of anvil (400) and the interior of knife member (340).

As shown in FIG. 3, anvil (400) of the present example includes a breakable washer (417) within annular recess (418). This washer (417) is broken by knife member (340) when knife member (340) completes a full distal range of motion from the position shown in FIG. 13C to the position shown in FIG. 13D. The drive mechanism for knife member (340) may provide an increasing mechanical advantage as knife member (340) reaches the end of its distal movement, thereby providing greater force by which to break washer (417). Of course, breakable washer (417) may be omitted entirely in some versions. In versions where washer (417) is included, washer (417) may also serve as a cutting board for knife member (340) to assist in cutting of tissue. Such a cutting technique may be employed in addition to or in lieu of the above-noted shearing action between inner edge (416) and cutting edge (342).

As staple driver member (350) translates distally from the position shown in FIG. 13C to the position shown in FIG. 13D, staple driver member (350) drives staples (90) through the tissue of tubular anatomical structures (20, 40) and into staple forming pockets (414) of anvil (400). Staple forming pockets (414) deform the driven staples (90) into a "B" shape as is known in the art. The formed staples (90) thus secure the ends of tissue together, thereby coupling tubular anatomical structure (20) with tubular anatomical structure (40).

Figure 13E:
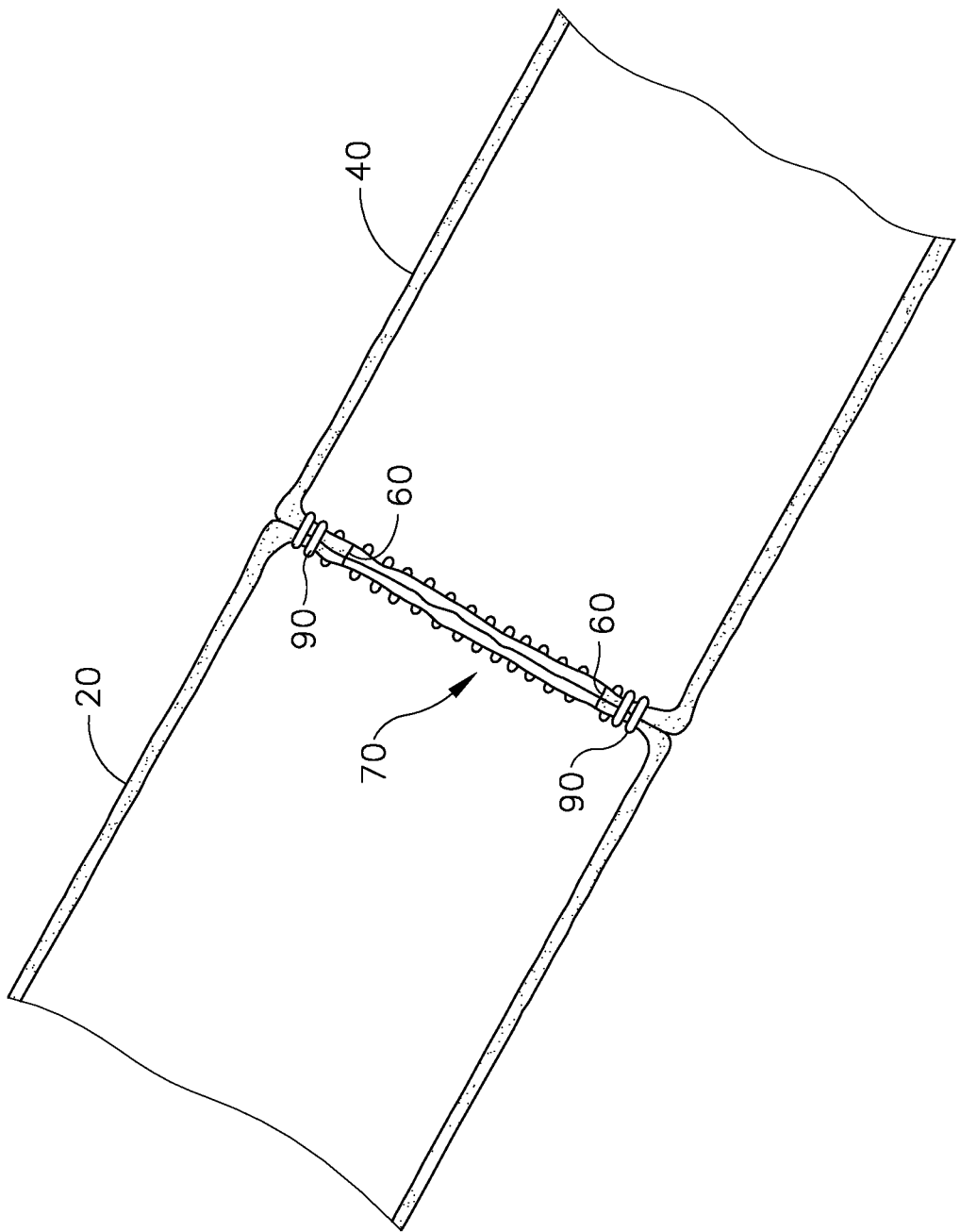
FIG. 13E depicts a cross-sectional side view of the first and second sections of the digestive tract of FIG. 13A joined together at an end-to-end anastomosis.

After the operator has actuated stapling head assembly (300) as shown in FIG. 13D, the operator rotates knob (130) to drive anvil (400) distally away from stapling head assembly (300), increasing the gap distance (d) to facilitate release of the tissue between surfaces (412, 322). The operator then removes instrument (10) from the patient, with anvil (400) still secured to trocar (330). Referring back to the example where the tubular anatomical structures (20, 40) comprise sections of a patient's colon, instrument (10) may be removed via the patient's rectum. With instrument (10) removed, the tubular anatomical structures (20, 40) are left secured together by two annular arrays of staples (90) at an anastomosis (70) as shown in FIG. 13E. The inner diameter of the anastomosis (70) is defined by the severed edge (60) left by knife member (340).

II. Exemplary Trigger Circuit with Immunity to Liquid Ingress

Those of ordinary skill in the art will recognize that, during normal use of instrument (10), at least certain portions of instrument (10) may be exposed to various fluids, including but not limited to patient bodily fluids, saline, etc. By way of example only, the regions of instrument (10) that may be most susceptible to liquid ingress may include stapling head assembly (300) and features at or near the underside of handle assembly (100), where liquid may tend to gather after running down shaft assembly (200). Those of ordinary skill in the art will also recognize that some electrical circuit components may experience compromised performance when such electrical circuit components are exposed to liquids. For instance, liquids may compromise the functioning of some electrical circuits and circuit components. In the context of a surgical instrument like instrument (10), a compromised circuit may cause a feature (e.g., motor (160) and thus stapling head assembly (300)) to activate prematurely, which may provide an undesirable outcome. It may therefore be desirable to provide a version of instrument (10) where ingress of liquid onto certain electrical circuit components will not compromise the performance of such electrical circuits and circuit components by causing premature activation or other undesirable effects.

While the following examples are provided in the context of a variation of instrument (10), the same teachings may be readily incorporated into various other kinds of surgical instruments. Other kinds of instruments to which the below teachings may be applied will be apparent to those of ordinary skill in the art.

Figure 14:
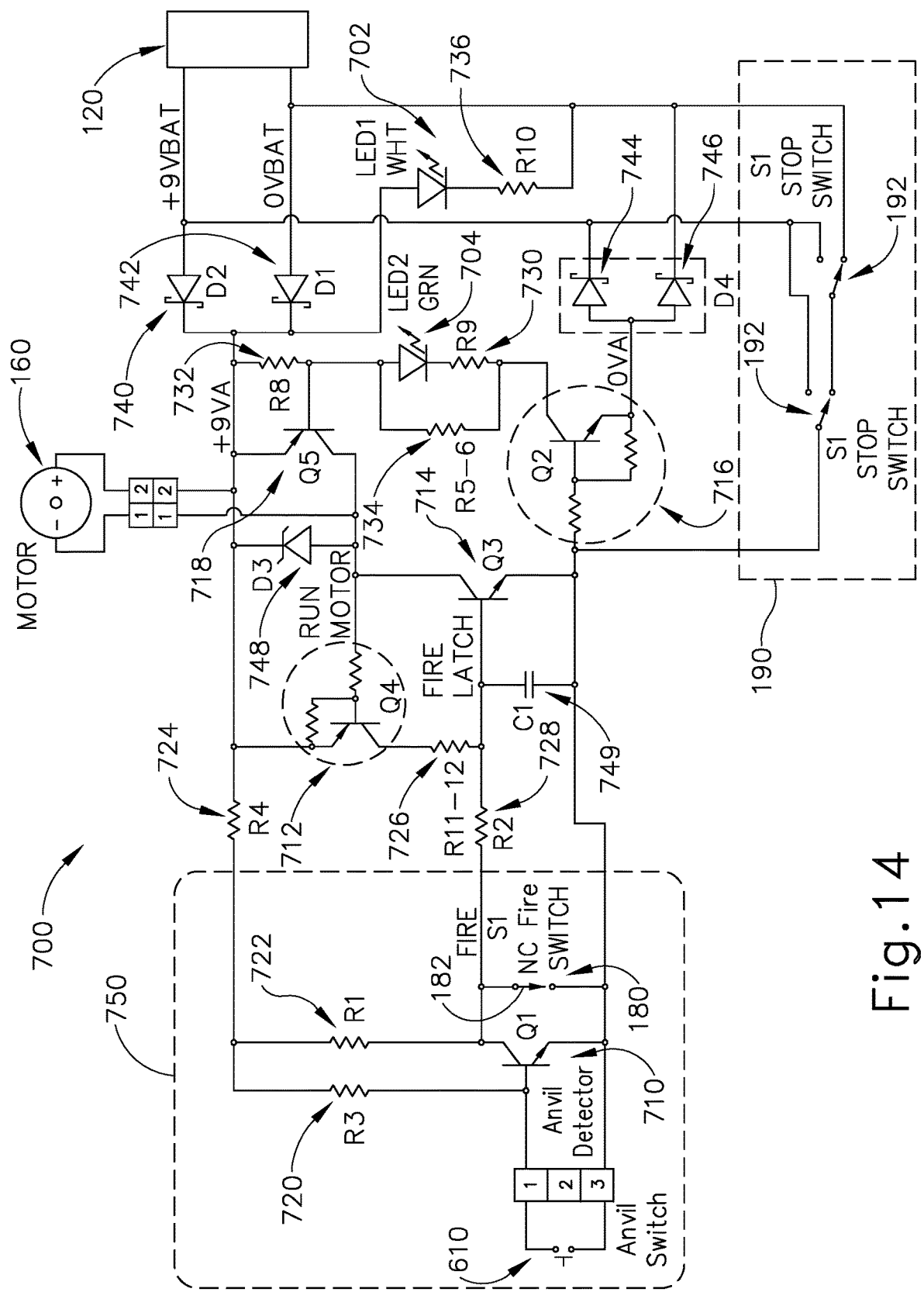
FIG. 14 depicts a schematic view of an exemplary circuit that may be incorporated into the instrument of FIG. 1.

FIG. 14 shows an exemplary control circuit (700) that may be incorporated into instrument (10). Circuit (700) is configured such that ingress of liquid onto dome switch (610) and motor activation module (180) will not compromise the performance of dome switch (610), motor activation module (180), or motor stop module (190). Dome switch (610) and motor activation module (180) are thus within a liquid-immune region (750) of circuit (700). As shown, circuit (700) of this example includes several transistors (710, 712, 714, 716, 718), several resistors (720, 722, 724, 726, 728, 730, 732, 734, 736), several schottky diodes (740, 742, 744, 746), a zener diode (748), and a capacitor (749). As also shown, battery pack (120), motor (160), motor activation module (180), switch buttons (192), dome switch (610), and LEDs (702, 704) are also incorporated into circuit (700).

In the present example, transistor (710), motor activation module (180), and resistors (720, 722) are all located within liquid-immune region (750) of circuit (700). Transistor (710) of the present example has a relatively low voltage threshold and is in communication with dome switch (610), motor activation module (180), and other components that are ultimately coupled with motor (160). In the present example, switch (182) of motor activation module (180) is configured such that switch (182) is held in a closed state by default. Thus, when paddle (158) engages motor activation module (180) in response to the operator pivoting firing trigger (150), paddle (158) transitions switch (182) of motor activation module (180) from a closed state to an open state.

Transistor (710) and the associated components of circuit (700) are configured to provide activation of motor (160) only when the switch of motor activation module (180) is in the open state (which would indicate that firing trigger (150) has been fully actuated) and when dome switch (610) is in the closed state (which would indicate that anvil (400) is properly coupled with trocar (330)). Thus, motor (160) will not be activated when the switch of motor activation module (180) is in the closed state (which would indicate that firing trigger (150) has not been fully actuated), even if dome switch (610) is in a closed state. Similarly, motor (160) will not be activated when dome switch (610) is in an open state (which would indicate that anvil (400) is not properly coupled with trocar (330)), even if the switch of motor activation module (180) is in the open state.

Those of ordinary skill in the art will recognize that a switch that is flooded with liquid may tend to be compromised, which may prematurely produce the effect of a closed switch. Thus, in alternative versions of circuit (700) where motor (160) is activated upon the transition of the switch of motor activation module (180) from an open state to a closed state, liquid ingress may compromise the switch to thereby effectively provide a closed state before firing trigger (150) is actuated. In other words, in alternative versions of circuit (700) where motor (160) is activated upon the transition of the switch of motor activation module (180) from an open state to a closed state, liquid ingress may result in premature activation of motor (160) and thus stapling head assembly (300). However, by requiring the switch of motor activation module (180) to be in an open state to provide activation of motor (160), circuit (700) of the present example prevents motor (160) and thus stapling head assembly (300) from being activated prematurely by liquid ingress.

When dome switch (610) is in an open state (i.e., when anvil (400) has not actuated dome switch (610) as described above), transistor (710) acts as a closed switch ("on"). When dome switch (610) is in a closed state (i.e., when anvil (400) has actuated dome switch (610) as described above), transistor (710) will behave as an open switch ("off"). Those of ordinary skill in the art will recognize that the voltage threshold of transistor (714) is equal to or greater than 0.7V because the emitter (the point at which transistors (714, 716) are connected) is connected to 0V of the battery. When the point at which capacitor (749), resistors (728, 726), and transistor (714) connect exceeds this threshold, transistor (714) will act a closed switch ("on"), thereby allowing motor (160) to activate.

Transistor (714) has a relatively low voltage threshold in the present example. Transistor (714) is thus capable of recognizing an open state of switch (182) of motor activation module (180), even if motor activation module (180) is flooded with electrically conductive liquid, due to the fact that the liquid provides enough resistivity that it does not create an equivalency to a closed switch. The liquid's resistivity will lower the voltage but not to a level below the low voltage threshold of transistor (710), thus allowing the transistor (710) to recognize that switch (182) has been opened.

In addition to, or as an alternative to, providing the configuration of circuit (700) described above, various electrical components may be coated with a liquid-impermeable coating to provide at least some degree of immunity to liquid ingress. For instance, in some versions, one or more printed circuit boards of circuit (700) (e.g., a circuit board to which LEDs (702, 704) are mounted) may be coated with a liquid-impermeable coating. In addition, or in the alternative, either or both of LEDs (702, 704) may be coated with a liquid-impermeable coating. Other features of circuit (700) that may be coated with a liquid-impermeable coating will be apparent to those of ordinary skill in the art in view of the teachings herein.

In some versions where a liquid-impermeable coating is used on one or more components of circuit (700), the liquid-impermeable coating may comprise an ultraviolet-cured urethane coating. In some versions, the liquid-impermeable coating is transparent. By making the coating transparent, this may preserve legibility of coated features that are intended to be viewed (e.g., either or both of LEDs (702, 704)). Moreover, in versions where one or both of LEDs (702, 704) is/are coated, use of a transparent coating may prevent the light emitted from the coated LED (702, 704) from being transmitted along the coating (i.e., "bleeding). Other various suitable materials that may be used to provide such coatings, and various methods that may be used to apply such coatings, will be apparent to those of ordinary skill in the art in view of the teachings herein.

III. Exemplary Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a body; (b) a shaft assembly extending distally from the body, wherein the shaft assembly has a distal end; (c) an end effector at the distal end of the shaft assembly, wherein the end effector is operable to operate on tissue; (d) an activation circuit, wherein the activation circuit comprises: (i) an end effector driver, wherein the end effector driver is operable to drive the end effector to perform an operation on tissue, and (ii) a driver activation switch, wherein the driver activation switch is configured to transition between an open state and a closed state, wherein the end effector driver is configured to activate in response to the driver activation switch transitioning to the open state, wherein the end effector driver is configured to not activate in response to the driver activation switch being in the closed state; and (e) a user input feature operable to transition between a non-actuated state and an actuated state, wherein the driver activation switch is configured to remain in the closed state when the user input feature is in the non-actuated state, wherein the driver activation switch is configured to transition from the closed state to the open state in response to the user input feature transitioning from the non-actuated state to the actuated state.

Example 2

The apparatus of Example 1, wherein the end effector comprises a stapling head assembly, wherein the stapling head assembly is operable to apply staples to tissue.

Example 3

The apparatus of Example 2, wherein the end effector further comprises a knife member operable to cut tissue.

Example 4

The apparatus of any one or more of Examples 2 through 3, wherein the stapling head assembly is operable to apply at least one annular row of staples to tissue.

Example 5

The apparatus of any one or more of Examples 2 through 4, wherein the end effector further comprises an anvil, wherein the anvil is operable to retract proximally relative to the stapling head assembly.

Example 6

The apparatus of Example 5, further comprising an anvil sensor, wherein the anvil sensor is configured to sense a position of the anvil in relation to the stapling head assembly.

Example 7

The apparatus of Example 6, wherein the activation circuit is further configured to prevent activation of the end effector driver unless the anvil sensor senses the anvil being located at or proximal to a predetermined longitudinal position relative to the stapling head assembly.

Example 8

The apparatus of any one or more of Examples 1 through 7, wherein the end effector driver comprises a motor.

Example 9

The apparatus of any one or more of Examples 1 through 8, wherein the user input feature comprises a trigger, wherein the trigger is movable from the non-actuated state to the actuated state.

Example 10

The apparatus of Example 9, wherein the trigger includes a paddle, wherein the paddle is configured to contact the driver activation switch when the trigger is moved to the actuated state to thereby transition the driver activation switch from the closed state to the open state.

Example 11

The apparatus of any one or more of Examples 1 through 10, wherein the activation circuit further comprises a low voltage threshold transistor in communication with the driver activation switch, wherein the low voltage threshold transistor is further in communication with the end effector driver.

Example 12

The apparatus of Example 11, wherein the low voltage threshold transistor is operable to recognize an open state of the driver activation switch when the driver activation switch is flooded with liquid.

Example 13

The apparatus of any one or more of Examples 1 through 12, further comprising at least one electronic component coated with a liquid impermeable coating.

Example 14

The apparatus of Example 13, wherein the at least one electronic component comprises a printed circuit board.

Example 15

The apparatus of any one or more of Examples 13 through 14, wherein the at least one electronic component comprises an LED.

Example 16

The apparatus of any one or more of Examples 13 through 15, wherein the liquid impermeable coating comprises ultraviolet cured urethane.

Example 17

The apparatus of any one or more of Examples 13 through 16, wherein the liquid impermeable coating is transparent.

Example 18

An apparatus comprising: (a) a body; (b) a shaft assembly extending distally from the body, wherein the shaft assembly has a distal end; (c) a stapling head assembly at the distal end of the shaft assembly, wherein the stapling head assembly is operable to apply staples to tissue and sever tissue; (d) an activation circuit, wherein the activation circuit comprises: (i) a motor, wherein the motor is operable to drive the stapling head assembly to apply staples to tissue and sever tissue, and (ii) a motor activation switch, wherein the motor activation switch is configured to transition between an open state and a closed state, wherein the motor is configured to activate in response to the motor activation switch transitioning from the closed state to the open state, wherein the motor is configured to not activate in response to the motor activation switch being in the closed state; and (e) a firing trigger operable to transition between a non-actuated state and an actuated state, wherein the motor activation switch is configured to remain in the closed state when the firing trigger is in the non-actuated state, wherein the motor activation switch is configured to transition from the closed state to the open state in response to the firing trigger transitioning from the non-actuated state to the actuated state.

Example 19

The apparatus of Example 18, further comprising: (a) an anvil, wherein the anvil is operable to retract proximally relative to the stapling head assembly; and (b) an anvil sensor, wherein the anvil sensor is configured to sense a position of the anvil in relation to the stapling head assembly; wherein the activation circuit further comprises a transistor coupled with the anvil sensor and the motor activation switch, wherein the transistor is configured to provide activation of the motor in response to the combination of the following: (i) the anvil sensor sensing the anvil being located at or proximal to a predetermined longitudinal position relative to the stapling head assembly, and (ii) the motor activation switch being in the open state; wherein the transistor is further configured to prevent activation of the motor in response to either of the following: (i) the anvil sensor not sensing the anvil being located at or proximal to a predetermined longitudinal position relative to the stapling head assembly, or (ii) the motor activation switch being in the closed state.

Example 20

A method of operating a surgical instrument, the method comprising: (a) positioning an end effector of a surgical instrument in a patient; (b) actuating a user input feature to transition the user input feature from a non-actuated state to an actuated state; (c) transitioning a driver activation switch from a closed state to an open state in response to the user input feature being actuated to the actuated state; (d) activating an end effector driver in response to the driver activation switch transitioning from the closed state to the open state; and (e) driving the end effector to operate on tissue in the patient in response to activation of the end effector driver.

IV. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

At least some of the teachings herein may be readily combined with one or more teachings of U.S. Pat. No. 7,794,475, entitled "Surgical Staples Having Compressible or Crushable Members for Securing Tissue Therein and Stapling Instruments for Deploying the Same," issued Sep. 14, 2010, the disclosure of which is incorporated by reference herein; U.S. Pub. No. 2014/0151429, entitled "Trans-Oral Circular Anvil Introduction System with Dilation Feature," published Jun. 5, 2014, issued as U.S. Pat. No. 9,572,573 on Feb. 21, 2017, the disclosure of which is incorporated by reference herein; U.S. Pub. No. 2014/0144968, entitled "Surgical Staple with Integral Pledget for Tip Deflection," published May 29, 2014, issued as U.S. Pat. No. 9,289,207 on Mar. 22, 2016, the disclosure of which is incorporated by reference herein; U.S. Pub. No. 2014/0158747, entitled "Surgical Stapler with Varying Staple Widths along Different Circumferences," published Jun. 12, 2014, now abandoned, the disclosure of which is incorporated by reference herein; U.S. Pub. No. 2014/0144969, entitled "Pivoting Anvil for Surgical Circular Stapler," published May 29, 2014, issued as U.S. Pat. No. 9,498,222 on Nov. 22, 2016, the disclosure of which is incorporated by reference herein; U.S. Pub. No. 2014/0151430, entitled "Circular Anvil Introduction System with Alignment Feature," published Jun. 5, 2014, issued as U.S. Pat. No. 9,724,100 on Aug. 8, 2017, the disclosure of which is incorporated by reference herein; U.S. Pub. No. 2014/0166717, entitled "Circular Stapler with Selectable Motorized and Manual Control, Including a Control Ring," published Jun. 19, 2014, issued as U.S. Pat. No. 9,532,783 on Jan. 3, 2017, the disclosure of which is incorporated by reference herein; U.S. Pub. No. 2014/0166728, entitled "Motor Driven Rotary Input Circular Stapler with Modular End Effector," published Jun. 19, 2014, issued as U.S. Pat. No. 9,597,081 on Mar. 21, 2017, the disclosure of which is incorporated by reference herein; and/or U.S. Pub. No. 2014/0166718, entitled "Motor Driven Rotary Input Circular Stapler with Lockable Flexible Shaft," published Jun. 19, 2014, issued as U.S. Pat. No. 9,463,022 on Oct. 11, 2016, the disclosure of which is incorporated by reference herein. Various suitable ways in which such teachings may be combined will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK® bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a body;
   (b) a shaft assembly extending distally from the body, wherein the shaft assembly has a distal end;
   (c) an end effector at the distal end of the shaft assembly, wherein the end effector is operable to operate on tissue;
   (d) an activation circuit, wherein the activation circuit comprises:
      (i) an end effector driver, wherein the end effector driver is operable to drive the end effector to perform an operation on tissue, and
      (ii) a driver activation switch, wherein the driver activation switch is configured to transition between an open state and a closed state, wherein the end effector driver is configured to activate in response to the driver activation switch being in the open state, wherein the end effector driver is configured to not activate in response to the driver activation switch being in the closed state; and
   (e) a user input feature operable to transition between a non-actuated state and an actuated state, wherein the driver activation switch is configured to remain in the closed state when the user input feature is in the non-actuated state, wherein the driver activation switch is configured to transition from the closed state to the open state in response to the user input feature transitioning from the non-actuated state to the actuated state.

2. The apparatus of claim 1, wherein the end effector comprises a stapling head assembly, wherein the stapling head assembly is operable to apply staples to tissue.

3. The apparatus of claim 2, wherein the end effector further comprises a knife member operable to cut tissue.

4. The apparatus of claim 2, wherein the stapling head assembly is operable to apply at least one annular row of staples to tissue.

5. The apparatus of claim 2, wherein the end effector further comprises an anvil, wherein the anvil is operable to retract proximally relative to the stapling head assembly.

6. The apparatus of claim 5, further comprising an anvil sensor, wherein the anvil sensor is configured to sense a position of the anvil in relation to the stapling head assembly.

7. The apparatus of claim 6, wherein the activation circuit is further configured to prevent activation of the end effector driver unless the anvil sensor senses the anvil being located at or proximal to a predetermined longitudinal position relative to the stapling head assembly.

8. The apparatus of claim 1, wherein the end effector driver comprises a motor.

9. The apparatus of claim 1, wherein the user input feature comprises a trigger, wherein the trigger is movable from the non-actuated state to the actuated state.

10. The apparatus of claim 9, wherein the trigger includes a paddle, wherein the paddle is configured to contact the driver activation switch when the trigger is moved to the actuated state to thereby transition the driver activation switch from the closed state to the open state.

11. The apparatus of claim 1, wherein the activation circuit further comprises a low voltage threshold transistor in communication with the driver activation switch, wherein the low voltage threshold transistor is further in communication with the end effector driver.

12. The apparatus of claim 11, wherein the low voltage threshold transistor is operable to recognize an open state of the driver activation switch when the driver activation switch is flooded with liquid.

13. The apparatus of claim 1, further comprising at least one electronic component coated with a liquid impermeable coating.

14. The apparatus of claim 13, wherein the at least one electronic component comprises a printed circuit board.

15. The apparatus of claim 13, wherein the liquid impermeable coating comprises ultraviolet cured urethane.

16. The apparatus of claim 1, wherein the driver activation switch is enclosed within the body.

17. An apparatus comprising:
(a) a body;
(b) a shaft assembly extending distally from the body, wherein the shaft assembly has a distal end;
(c) a stapling head assembly at the distal end of the shaft assembly, wherein the stapling head assembly is operable to apply staples to tissue and sever tissue;
(d) an activation circuit, wherein the activation circuit comprises:
(i) a motor, wherein the motor is operable to drive the stapling head assembly to apply staples to tissue and sever tissue, and
(ii) a motor activation switch, wherein the motor activation switch is configured to transition between an open state and a closed state, wherein the motor is configured to activate in response to the motor activation switch being in the open state, wherein the motor is configured to not activate in response to the motor activation switch being in the closed state; and
(e) a firing trigger operable to transition between a non-actuated state and an actuated state, wherein the motor activation switch is configured to remain in the closed state when the firing trigger is in the non-actuated state, wherein the motor activation switch is configured to transition from the closed state to the open state in response to the firing trigger transitioning from the non-actuated state to the actuated state.

18. The apparatus of claim 17, further comprising:
(a) an anvil, wherein the anvil is operable to retract proximally relative to the stapling head assembly; and
(b) an anvil sensor, wherein the anvil sensor is configured to sense a position of the anvil in relation to the stapling head assembly;
wherein the activation circuit further comprises a transistor coupled with the anvil sensor and the motor activation switch, wherein the transistor is configured to provide activation of the motor in response to the combination of the following:
(i) the anvil sensor sensing the anvil being located at or proximal to a predetermined longitudinal position relative to the stapling head assembly, and
(ii) the motor activation switch being in the open state;
wherein the transistor is further configured to prevent activation of the motor in response to either of the following:
(i) the anvil sensor not sensing the anvil being located at or proximal to a predetermined longitudinal position relative to the stapling head assembly, or
(ii) the motor activation switch being in the closed state.

19. The apparatus of claim 17, wherein the body defines an interior having a liquid-immune region, wherein the motor activation switch is positioned within the liquid-immune region.

20. An apparatus comprising:
(a) a body;
(b) a shaft assembly extending distally from the body, wherein the shaft assembly has a distal end;
(c) an end effector at the distal end of the shaft assembly, wherein the end effector is operable to operate on tissue, wherein the end effector comprises:
(i) a stapling head assembly, wherein the stapling head assembly is operable to apply staples to tissue, and
(ii) an anvil, wherein the anvil is movable toward the stapling head assembly to clamp tissue therebetween;
(d) an activation circuit, wherein the activation circuit comprises:
(i) an end effector driver, wherein the end effector driver is operable to drive the end effector to perform an operation on tissue, and
(ii) a driver activation switch, wherein the driver activation switch is enclosed within the body, wherein the driver activation switch is configured to transition between an open state and a closed state, wherein the end effector driver is configured to activate in response to the driver activation switch being in the open state, wherein the end effector driver is configured to not activate in response to the driver activation switch being in the closed state; and
(e) an anvil sensor, wherein the anvil sensor is configured to communicate to the activation circuit a position of the anvil in relation to the stapling head assembly.

* * * * *